United States Patent
Harper et al.

(10) Patent No.: US 9,212,430 B1
(45) Date of Patent: *Dec. 15, 2015

(54) METHOD FOR THE ELECTRO-ADDRESSABLE FUNCTIONALIZATION OF ELECTRODE ARRAYS

(75) Inventors: Jason C. Harper, Rio Rancho, NM (US); Ronen Polsky, Albuquerque, NM (US); Shawn M. Dirk, Albuquerque, NM (US); David R. Wheeler, Albuquerque, NM (US); Dulce C. Arango, Albuquerque, NM (US); Susan M. Brozik, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 939 days.

This patent is subject to a terminal disclaimer.

(21) Appl. No.: 11/930,267

(22) Filed: Oct. 31, 2007

(51) Int. Cl.
*C25D 9/02* (2006.01)
*C07C 245/20* (2006.01)
*C07F 5/02* (2006.01)
*C40B 20/02* (2006.01)

(52) U.S. Cl.
CPC .............. *C25D 9/02* (2013.01); *C07C 245/20* (2013.01); *C07F 5/025* (2013.01); *C40B 20/02* (2013.01)

(58) Field of Classification Search
USPC ........................................ 204/403.01, 403.03
See application file for complete search history.

(56) References Cited

U.S. PATENT DOCUMENTS

| | | |
|---|---|---|
| 5,217,112 A | 6/1993 | Almon |
| 6,281,006 B1 | 8/2001 | Heller et al. |
| 6,652,720 B1 | 11/2003 | Mansouri et al. |
| 7,250,147 B2 | 7/2007 | Tour et al. |
| 7,314,505 B1 | 1/2008 | Wheeler et al. |
| 7,550,071 B1 | 6/2009 | Dirk et al. |
| 7,736,484 B2 | 6/2010 | Bureau et al. |
| 2007/0158212 A1 | 7/2007 | Filanovsky |
| 2010/0000881 A1 | 1/2010 | Franzen et al. |

OTHER PUBLICATIONS

Vase et al., Langmuir, 2005, 21:8085-8089.*
Vase et al., Langmuir, 2008, 24:182-188.*
Wang et al. (Diamond & Related Materials, 2006, 15:279-284).*
Laforgue et al. (Langmuir, 2005, 21:6855-6865).*
Guozhen Liu et al, "An Interface Comprising Molecular Wires and Poly(ethylene glycol) Spacer Units Self-Assembled on Carbon Electrodes for Studies of Protein Electrochemistry", American Chemical Society, 2006, vol. 22, No. 417, pp. 7421-7430.
Christian Bourdillon et al, "Immobilization of glucose oxidase on a carbon surface derivatized by electrochemical reduction of diazonium salts", J. Electroanal. Chem, 1992, vol. 336, pp. 113-123.
Michel Delamar et al, "Covalent Modification of Carbon Surfaces by Grafting of Functionalized Aryl Radicals Produced from electrochemical Reduction of Diazonium Salts", Journal of the American Chemical Society, vol. 114 (1992) pp. 5883-5884.

(Continued)

*Primary Examiner* — Jeremy C Flinders
(74) *Attorney, Agent, or Firm* — Helen S. Baca

(57) ABSTRACT

A method for preparing an electrochemical biosensor uses bias-assisted assembly of unreactive -onium molecules on an electrode array followed by post-assembly electro-addressable conversion of the unreactive group to a chemical or biological recognition group. Electro-addressable functionalization of electrode arrays enables the multi-target electrochemical sensing of biological and chemical analytes.

15 Claims, 16 Drawing Sheets

(56) References Cited

OTHER PUBLICATIONS

Murielle Dequaire et al, "Biotinylation of Screen-Printed Carbon Electrodes through the Electrochemical Reduction of the Diazonium Salt of p-Aminobenzoyl Biocytin", Journal of the American Chemical Society, 1999, vol. 121, pp. 6946-6947.
Jason C. Harper et al, "Electroaddressable Selective Functionalization of Electrode Arrays: Catalytic NADH Detection Using Aryl Diazonium Modified Gold Electrodes", Electroanalysis, 2007, vol. 19, No. 12 pp. 1268-1274.
Alexis Laforgue et al, "Characterization of the Deposition of Organic Molecules at the Surface of Gold by the Electrochemical Reduction of Aryldiazonium Cations," Langmuir, 2005, vol. 21, pp. 6855-6865.
Chang-Soo Lee et al, "Electrically Addressable Biomolecular Functionalization of Carbon Nanotube and Carbon Nanofiber Electrodes", Nano letters, 2004, vol. 4, No. 9, pp. 1713-1716.
Guozhen Liu et al, "Diazonium salts: Stable monolayers on gold electrodes for sensing applications", J. Electroanal. Chem, 2007, vol. 600, pp. 335-344.
Chao Yung Fan et al, "Protein Pattern Assembly by Active Control of a Triblock Copolymer Monolayer", American Chemical Society, Nano Letters, vol. 6, No. 12, 2006 pp. 2763-2767.
A Shabani et al, "DNA immobilization onto electrochemically functionalized Si(100) surfaces", Talanta, vol. 70 (2006) pp. 615-623.
Michael P. Stewart et al, "Direct Covalent Grafting of Conjugated Molecules onto Si, GaAs, and Pd Surfaces from Aryldiazonium Salts" Journal of the American Chemical Society, 2004, vol. 126, pp. 370-378.
U.S. Appl. No. 13/183,099, filed Jul. 14, 2011, Brozik et al.
Adenier A et al., "Formation of polyphenylene films on metal electrodes by electrochemical reduction of benzenediazonium salts," *Chem. Mater.* 2006;18:2021-9.
Allongue P et al., "Covalent modification of carbon surfaces by aryl radicals generated from the electrochemical reduction of diazonium salts," *J. Am. Chem. Soc.* 1997;119:201-7.
Allongue P et al., "Phenyl layers of H—Si(111) by electrochemical reduction by diazonium salts: monolayer versus multilayer formation," *J. Electroanal. Chem.* 2003;550-551:161-74.
Anariba F et al., "Mono- and multilayer formation of diazonium reduction on carbon surfaces monitored with atomic force microscopy 'scratching'," *Anal. Chem.* 2003;75:3837-44.
Bernard MC et al., "Organic layers bonded to industrial, coinage, and noble metals through electrochemical reduction of aryldiazonium salts," *Chem. Mater.* 2003;15:3450-62.
Boukerma K et al., "X-ray photoelectron spectroscopy evidence for the covalent bond between an iron surface and aryl groups attached by the electrochemical reduction of diazonium salts," *Langmuir* 2003;19(15):6333-5.
Bozic RG et al., "Square wave voltammetric detection of 2,4,6-trinitrotoluene and 2,4-dinitrotoluene on a gold electrode modified with self-assembled monolayers," *Sens. Actuat. B* 2008;133:509-15.
Brooksby PA et al., "Multilayer nitroazobenzene films covalently attached to carbon: an AFM and electrochemical study," *J. Phys. Chem. B* 2005;109:8791-8.
Brooksby PA et al., "Nanoscale patterning of flat carbon surfaces by scanning probe lithography and electrochemistry," *Langmuir* 2005;21:1672-5.
Bullen D et al., "Parallel dip-pen nanolithography with arrays of individually addressable cantilevers," *Appl. Phys. Lett.* Feb. 2004;84(5):789-91.
Buriak JM, "Organometallic chemistry on silicon and germanium surfaces," *Chem. Rev.* May 2002;102(5):1271-308.
Corgier BP et al., "Diazonium-protein adducts for graphite electrode microarrays modification: direct and addressed electrochemical immobilization," *J. Am. Chem. Soc.* 2005;127:18328-32.
Corgier BP et al., "Direct electrochemical addressing of immunoglobulins: Immuno-chip on screen-printed microarray," *Biosens. Bioelectron.* 2007;22:1522-6.

Cosnier S et al., "Biomolecule immobilization on electrode surfaces by entrapment or attachment to electrochemically polymerized films. A review," *Biosens. Bioelectron.* 1999;14:443-56.
Coulon E et al., "Electrochemical attachment of organic groups to carbon felt surfaces," *Langmuir* 2001;17:7102-6.
Degani Y et al., "Direct electrical communication between chemically modified enzymes and metal electrodes. 2. Methods for bonding electron-transfer relays to glucose oxidase and D-amino-acid oxidase," *J. Am. Chem. Soc.* 1988;110:2615-20.
Dirk SM et al., "Potential-directed assembly of aryl iodonium salts onto silicon {100} hydride terminated and platinum surfaces," *Langmuir* Nov. 2005;21(24):10899-901.
Downard AJ et al., "Microscale patterning of organic films on carbon surfaces using electrochemistry and soft lithography," *Langmuir* 2006;22:10739-46.
Edwards TL et al., "A parallel microfluidic channel fixture fabricated using laser ablated plastic laminates for electrochemical and chemiluminescent biodetection of DNA," *Biomicrofluidics* Dec. 2011;5(4):Article 044115 (14 pages).
Filanovsky B et al., "Carbon electrodes modified with $TiO_2$/metal nanoparticles and their application to the detection of trinitrotoluene," *Adv. Funct. Mater.* 2007;17:1487-92.
Gabriel S et al., "Electrografting of poly(ethylene glycol) acrylate: a one-step strategy for the synthesis of protein-repellant surfaces," *Angew. Chem. Int. Ed.* 2005;44:5505-9.
Ghilane J et al., "Indirect reduction of aryldiazonium salts onto cathodically activated platinum surfaces: formation of metal-organic structures," *Langmuir* 2005;21:6422-9.
Gill R et al., "Pt nanoparticles functionalized with nucleic acid act as catalytic labels for the chemiluminescent detection of DNA and proteins," *Small* 2006;2(8-9):1037-41.
Ginger DS et al., "The evolution of dip-pen nanolithography," *Angew. Chem. Int. Ed.* 2004;43:30-45.
Harper JC et al., "A multifunctional thin film Au electrode surface formed by consecutive electrochemical reduction of aryl diazonium salts," *Langmuir* 2009;25:3282-8.
Harper JC et al., "Maleimide-activated aryl diazonium salts for electrode surface functionalization with biological and redox-active molecules," *Langmuir* Mar. 4, 2008;24(5):2206-11.
Harper JC et al., "Selective immobilization of DNA and antibody probes on electrode arrays: simultaneous electrochemical detection of DNA and protein on a single platform," *Langmuir* Jul. 31, 2007;23(16):8285-7.
Hilmi A et al., "Electrochemical detectors prepared by electroless deposition for microfabricated electrophoresis chips," *Anal. Chem.* 2000;72:4677-82.
Hrapovic S et al., "Metallic nanoparticle-carbon nanotube composites for electrochemical determination of explosive nitroaromatic compounds," *Anal. Chem.* Aug. 2006;78(15):5504-12.
Hurley BL et al., "Covalent bonding of organic molecules to Cu and Al alloy 2024 T3 surfaces via diazonium ion reduction," *J. Electrochem. Soc.* 2004;151(5):B252-9.
Hurley PT et al., "Nanopatterning of alkynes on hydrogen-terminated silicon surfaces by scanning probe-induced cathodic electrografting," *J. Am. Chem. Soc.* 2003;125:11334-9.
Kariuki JK et al., "Formation of multilayers on glassy carbon electrodes via the reduction of diazonium salts," *Langmuir* 2001;17(19):5947-51.
Kong YT et al., "Direct electrochemistry of horseradish peroxidase bonded on a conducting polymer modified glassy carbon electrode," *Biosens. Bioelectron.* 2003;19:227-32.
Kosynkin DV et al., "Self-assembly of phenylene ethynylene diazonium salts on metal surfaces as potential molecular wires," *Mat. Res. Soc. Symp. Proc.* 2001;660:JJ3.5.1-JJ3.5.5.
Krämer S et al., "Scanning probe lithography using self-assembled monolayers," *Chem. Rev.* 2003;103:4367-418.
Lee CS et al., Supporting Information for "Electrically addressable biomolecular functionalization of carbon nanotube and carbon nanofiber electrodes, *Nano Lett.* 2004;4(9):1713" (6 pages, accessible at http://pubs.acs.org/doi/suppl/10.1021/nl048995x, last accessed Jan. 27, 2014).
Li Y et al., "Electrochemical AFM "Dip-pen" nanolithography," *J. Am. Chem. Soc.* 2001;123:2105-6.

(56) References Cited

OTHER PUBLICATIONS

Liu G et al., "The modification of glassy carbon and gold electrode with aryl diazonium salt: the impact of the electrode materials on the rate of heterogeneous electron transfer," *Chem. Phys.* 2005;319:136-46.

Liu YC et al., "Raman spectroscopic determination of the structure and orientation of organic monolayers chemisorbed on carbon electrode surfaces," *Anal. Chem.* 1997; 69:2091-7.

Lou X et al., "Electrografting of preformed aliphatic polyesters onto metallic surfaces," *Langmuir* 2002;18:2785-8.

Louault C et al., "The electrochemical grafting of a mixture of substituted phenyl groups at a glassy carbon electrode surface," *ChemPhysChem* 2008;9:1164-70.

Ni Y et al., "Simultaneous detection of nitrobenzene and nitro-substituted phenols by differential pulse voltammetry and chemometrics," *Anal. Chim. Acta* 2001;431:101-13.

Petrov P et al., "Functionalization of multi-walled carbon nanotubes by electrografting of polyacrylonitrile," *Macromol. Rapid Commun.* 2004;25:987-90.

Pinson J et al., "Attachment of organic layers to conductive or semiconductive surfaces by reduction of diazonium salts," *Chem. Soc. Rev.* May 2005;34(5):429-39.

Polsky R et al., "Diazonium-functionalized horseradish peroxidase immobilized via addressable electrodeposition: direct electron transfer and electrochemical detection," *Langmuir* 2007;23:364-6.

Polsky R et al., "Electrically addressable cell immobilization using phenylboronic acid diazonium salts," *Angew. Chem. Int. Ed. Engl.* 2008;47(14):2631-4.

Polsky R et al., "Electrically addressable diazonium-functionalized antibodies for multianalyte electrochemical sensor applications," *Biosens. Bioelectron.* Jan. 18, 2008;23(6):757-64.

Polsky R et al., "Multifunctional electrode arrays: towards a universal detection platform," *Electroanalysis* 2008;20(6):671-9.

Polsky R et al., "Nucleic acid-functionalized Pt nanoparticles: catalytic labels for the amplified electrochemical detection of biomolecules," *Anal. Chem.* 2006;78:2268-71.

Polsky R et al., "Reagentless electrochemical immunoassay using electrocatalytic nanoparticle-modified antibodies," *Chem. Commun.* (*Camb.*) Jul. 14, 2007;(26):2741-3.

Prodromidis MI et al., "Enzyme based amperometric biosensors for food analysis," *Electroanal.* 2002;14(4):241-61.

Riskin M et al., "Imprinting of molecular recognition sites through electropolymerization of functionalized Au nanoparticles: development of an electrochemical TNT sensor based on Π-donor-acceptor interactions," *J. Am. Chem. Soc.* 2008;130:9726-33.

Sakata T et al., "Anti-sticking effect of organic dielectric formed by electrodeposition in microelectromechanical-system structures," *Japan. J. Appl. Phys.* 2005;44(7B):5732-5.

Singh S, "Sensors—an effective approach for the detection of explosives," *J. Hazard. Mater.* 2007;144:15-28.

Solak AO et al., "Modified carbon surfaces as organic electrodes that exhibit conductance switching," *Anal. Chem.* 2003;75:296-305.

Tu R et al., "Amine-capped ZnS-$Mn^{2+}$ nanocrystals for fluorescence detection of trace TNT explosive," *Anal. Chem.* 2008;80:3458-65.

Uetsuka H et al., "Electrochemical grafting of boron-doped single-crystalline chemical vapor deposition diamond with nitrophenyl molecules," *Langmuir* 2007;23:3466-72.

Vase KH et al., "Covalent grafting of glassy carbon electrodes with diaryliodonium salts: new aspects," *Langmuir* 2007;23:3786-93.

Wang J et al., "Carbon nanotube-modified glassy carbon electrode for adsorptive stripping voltammetric detection of ultratrace levels of 2,4,6-trinitrotoluene," *Electrochem. Commun.* 2004;6:176-9.

Wang J et al., "Electrochemical sensing of explosives," *Electroanalysis* 2007;19(4):415-23.

Wang J et al., "On-line electrochemical monitoring of (TNT) 2,4,6-trinitrotoluene in natural waters," *Anal. Chim. Acta* 2003;485:139-44.

Wang J et al., "Real-time electrochemical monitoring: toward green analytical chemistry," *Acc. Chem. Res.* 2002;35:811-6.

Wang J et al., "Screen-printed voltammetric sensor for TNT," *Talanta* 1998;46:1405-12.

Wang J et al., "Single-channel microchip for fast screening and detailed identification of nitroaromatic explosives or organophosphate nerve agents," *Anal. Chem.* 2002;74:1187-91.

Wang J et al., "Surface functionalization of ultrananocrystalline diamond films by electrochemical reduction of aryldiazonium salts," *Langmuir* 2004;20:11450-6.

Yang CC et al., "Electrocatalytic reduction and determination of dissolved oxygen at a preanodized screen-printed carbon electrode modified with palladium nanoparticles," *Electroanal.* 2006;18(1):64-9.

Zhang HX et al., "Functionalized carbon nanotubes as sensitive materials for electrochemical detection of ultra-trace 2,4,6-trinitrotoluene," *Phys. Chem. Chem. Phys.* 2006;8:3567-72.

\* cited by examiner

US 9,212,430 B1

METHOD FOR THE ELECTRO-ADDRESSABLE FUNCTIONALIZATION OF ELECTRODE ARRAYS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to electrochemical biosensors and, in particular, to a method for the electro-addressable functionalization of electrode arrays that can be used for the multi-target electrochemical sensing of biological and chemical analytes.

BACKGROUND OF THE INVENTION

Biosensors make use of the interaction of biological molecules (biomolecules) as a means of sensing an external environment. Biosensors can be very selective, due to the highly specific interactions between biomolecules, for example antibodies and their antigens, cytokines and their cell-surface receptors, enzymes and their substrates, or nucleic acids with themselves or other molecules. The species being sensed in the environment is referred to as the analyte. Therefore, the analyte can be another biological molecule or a chemical that interacts with an immobilized chemical or biological (chem/bio) recognition molecule that has high selectivity for the target analyte. Further, signal transduction methods combined with amplification can provide biosensors with high sensitivity. These properties—selectivity and sensitivity—make biosensors particularly attractive as analytical devices.

A biosensor preferably can analyze multiple analytes simultaneously. Therefore, microarray technology has become an important tool for high throughput analysis of biological systems. See A. Kozarova et al., *J. Proteome Res.* 5, 1051 (2006); and J. Sobek et al., *Comb. Chem. High T. Sci.* 9, 365 (2006). The ability to selectively modify electrode surfaces of a microarray is a critical component in the development of bioelectronics, proteomic research, tissue engineering, clinical diagnostics, and chemical and biological sensing. Multi-analyte sensors require surface chemistries that are robust and allow for addressable functionalization with peptides, nucleic acids, proteins, and sensitive chemical groups onto closely spaced arrays. See I. Medintz, *Nature Mat.* 5, 842 (2006); and C. Y. Fan et al., *Nano Lett.* (2006).

Therefore, a need remains for a versatile surface chemistry capable of selective functionalization of an electrode array with controllable surface density, and which is compatible with chem/bio recognition element immobilization. Such chemistry would facilitate development and fabrication of complex surfaces allowing precise manipulation, detection, and quantification of chemical and biological compounds.

SUMMARY OF THE INVENTION

The present invention is directed to a method for preparing an electrochemical biosensor, comprising providing an electrode array comprising a plurality of conducting or semiconducting electrodes; assembling phenyl molecules having an unreactive group from an aryl-diazonium salt on the plurality of electrodes; and applying a bias voltage to at least one selected electrode of the electrode array to convert the unreactive group of the assembled phenyl molecules to a reactive group on the selected electrodes. The phenyl molecules can be assembled via bias-assisted electrodeposition from the aryl-diazonium salt. The reactive group can be converted, post-assembly, to a chemical or biological recognition group that has selectivity for a target analyte.

The resulting biosensor can be used to detect the target analyte(s) either directly (label-free) or indirectly (labeled or mediated). For example, the target analyte can be detected directly via electrochemical reaction between the modified electrode and the target analyte. Alternatively, the target can be detected by inducing a change in the electron transfer properties of the modified electrode upon target analyte binding to or interaction with the surface. Indirect detection can include subsequent binding of labels that include, but are not limited to, proteins, nanoparticles, beads, or any material that can directly or indirectly affect the electron transfer properties of the modified electrode surface.

The -onium molecule can comprise diazonium, iodonium, or sulfonium, and is preferably an aryl-diazonium. The unreactive group can comprise a nitro group or a boronic acid pinacol ester. The reactive group can comprise an amino, carboxyl, or boronic acid group. The chem/bio recognition molecule can comprise a native, modified, or synthetic biomolecule, such as an antibody, protein, enzyme, DNA, RNA, peptide, or whole cell, or a chemically sensitive group including pyrroloquinoline quinone (PQQ).

The direct electrically addressable activation of electrodes in an electrode array using -onium surface chemistry is highly suitable for electrochemical sensing. For example, the method can be used to selectively convert nitrophenyl diazonium modified electrodes to aminophenyl electrodes, activating the surface towards reactions that utilize the reactive amine groups. The activated electrodes can be readily functionalized using common amine coupling chemistry. The unactivated electrodes retain the nitro functional group and are protected from mild chemical reactions and non-specific absorption. Additionally, phenyl boronic acid pinacol ester diazonium modified electrodes can be deprotected chemically and reprotected with a 1-(4-methoxy-phenyl)-2-methyl-propane-1,2-diol (MPMP-diol) reprotection unit. This MPMP-diol can be removed electrochemically, providing a boronic acid surface that is active towards binding of saccharide groups. This interaction can be used to immobilize sugars, glycoproteins, or whole cells onto electrodes. The onium-based method of selective electrode functionalization can enable precise control of film thickness and degree of functionality for multi-analyte electrochemical biosensors.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

Diazonium molecules self assemble via an electron transfer mechanism on many conducting and semiconducting surfaces, such as silicon, carbon, and metals. The advantages of using diazonium chemistry include a highly stable covalent bond, ease of preparation and the ability to selectively modify conducting and semiconducting surfaces with the application of a potential bias. See Delamar et al., *J. Am. Chem. Soc.* 114, 5883 (1992); and Stewart et al., *J. Am. Chem. Soc.* 126, 27 (2004). Diazonium-modified electrodes have been used to immobilize many biomolecules including DNA, proteins, and peptides. See A. Shabani et al., *Talanta* 70, 615 (2006); C.-S. Lee et al., *Nano Lett.* 4, 1713 (2004); G. Liu and J. J. Gooding, *Langmuir* 22, 7421 (2006); M. Dequaire et al., *J. Am. Chem. Soc.* 121, 6946 (1999); C. Bourdillon et al., *J. Electroanal. Chem.* 336, 113 (1992); G. Z. Liu et al., *J. Electroanal. Chem.* 600, 335 (2007); and A. Laforgue et al., *Langmuir* 21, 6855 (2005). The utility of this technique for electrochemical analyte detection, sandwich electrochemical immunoassay, as well as the ability to individually and selectively address closely-spaced microelectrodes for multi-analyte detection in an array format has been demonstrated. Diazonium-modified protein electrodes have been used to detect $H_2O_2$ and cytokines as well as to construct multi-analyte immunosensors and to enable the simultaneous electrochemical detection of DNA and protein on the same electrode array. See U.S. patent application Ser. No. 10/984,569 to Dirk et al., filed Nov. 9, 2004; and U.S. patent application Ser. No. 11/762,414 to Polsky et al. filed Jun. 13, 2007; which are incorporated herein by reference.

Figure 1:
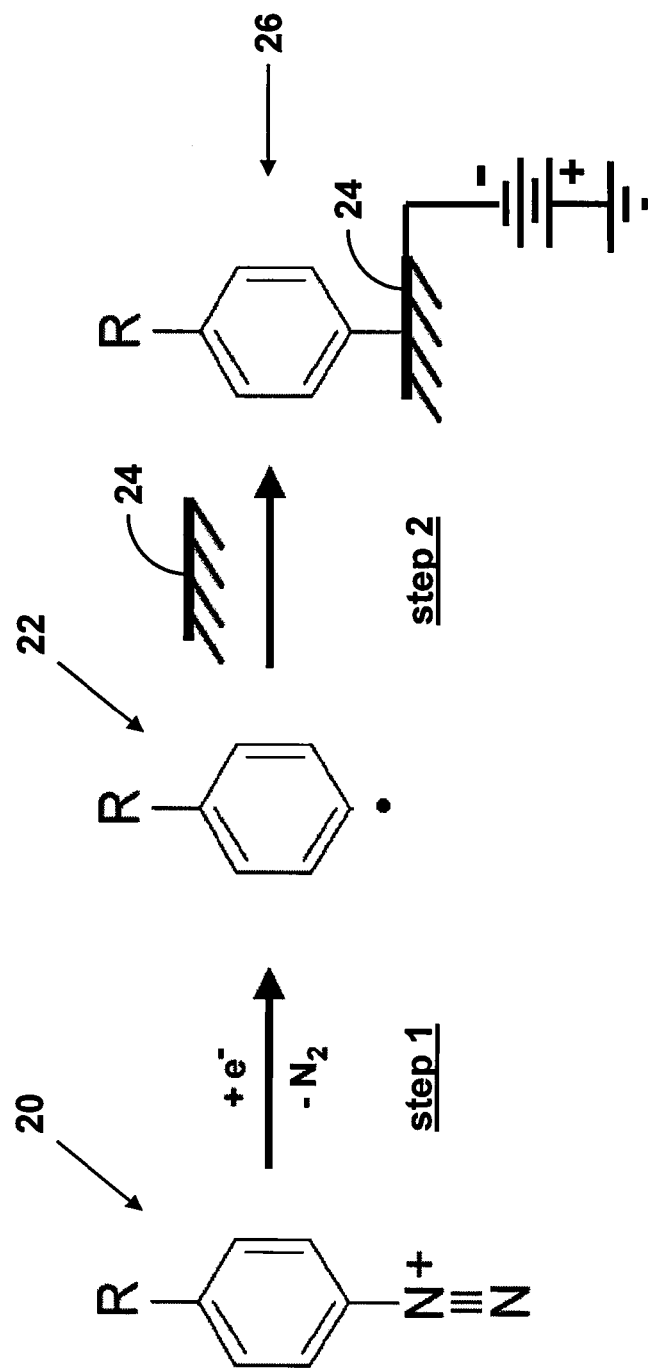
FIG. 1 shows a schematic illustration of the assembly of an aryl-diazonium molecule by direct electrochemical grafting to the surface of a conducting or semiconducting electrode.

In FIG. 1 is shown the self-assembly of an aryl-diazonium molecule by direct electrochemical grafting to the surface of a conducting or semiconducting electrode, according to the method of Stewart et al. A solution comprising an aryl-diazonium salt in an anhydrous solvent (e.g., acetonitrile) is provided. At step 1, electrochemical reduction of the diazonium salt 20 generates an aryl radical 22 with simultaneous loss of nitrogen. At step 2, the aryl radical 22 can then graft to the conducting or semiconducting surface 24 to provide a covalently bound phenyl monolayer 26, or multilayers. The assembly can be enhanced by applying a negative bias (as shown), or it can be blocked by applying a positive bias. Advantages to this approach are a highly stable surface, ease of preparation, and the ability to synthesize diazonium salts with a wide range of functional groups R. Further, the ability to create a diazonium-modified surface by the application of a potential bias enables the selective functionalization of closely-spaced, electrically addressable microelectrode surfaces.

Figure 2:
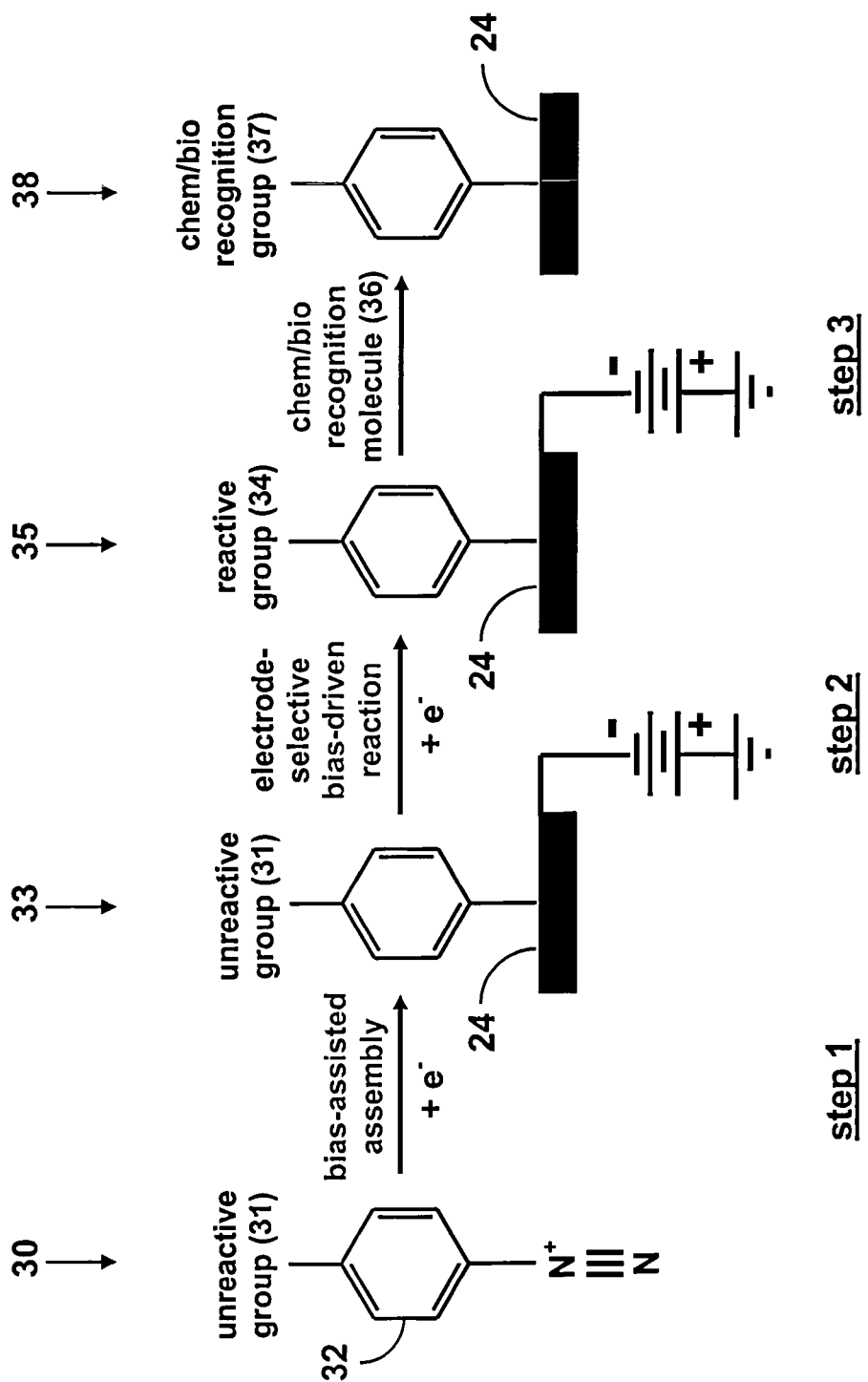
FIG. 2 shows a schematic illustration of a method to prepare an electrochemical biosensor comprising an electrode array that is selectively functionalized to detect a target analyte.

Preparation of a Biochemical Sensor Via
Electro-Addressable Conversion of an Unreactive to
a Reactive Group In FIG. 2 is shown a method of the present invention, wherein the functional group R can be an unreactive group that enables post-assembly electro-addressable conversion to or addition of a chemical or biological recognition group for detection of a target analyte. A solution comprising an -onium salt 30 having an electro-reducible or -oxidizable unreactive group 31 in a solvent is provided. Any -onium salt, such as diazonium, iodonium or sulfonium, that can graft to a conducting or semiconducting electrode and allows bias-driven reaction and surface functionalization can be used. The -onium salt is preferably an aryl-onium salt. The aryl-onium salt is preferably an aryl-diazonium salt, as will be used as an example to describe the invention hereinafter. The unreactive group 31 may be blocked, protected, or inactive towards given chemistries for binding or detecting chemical or biological molecules. The unreactive group can be located on any position on the phenyl ring 32 of the aryl-diazonium, and more than one unreactive group or differing groups can be located on a given phenyl ring. The conducting or semiconducting electrode 24 can be a bare conducting or semiconducting electrode or a substrate coated with a thin film or other surface modification, as long as diazonium grafting can occur.

At step 1, electrochemical reduction of the aryl-diazonium salt 30 generates an aryl radical (not shown) with simultaneous loss of nitrogen. The aryl radical can then graft to the electrode surface 24 to provide an unreactive bound diazonium electrode 33. This assembly can be assisted by applying a negative bias (as shown), or it can be blocked by applying a positive bias.

At step 2, the unreactive group 31 of the bound aryl-diazonium electrode 33 can be activated, replaced, converted, or deprotected to provide a reactive group 34 through an electrode-selective, bias-driven reaction. The unreactive bound diazonium molecule can be made reactive by negative biasing of the electrode 24, which electrochemically converts the unreactive (deactivated) group 31 to a different group (activated) 34 that is more reactive. One or more electrodes of a multi-electrode array can be biased to enable electro-addressable conversion of the selected inactive diazonium electrodes 33 to activated diazonium electrodes 35.

At step 3, a biological or chemical recognition molecule 36 can react with the reactive group 34 of the activated diazonium electrode 35 through specific coupling chemistries to provide a chemical or biological recognition group 37 on an electroactive diazonium electrode 38. The recognition molecule 36 can be any native, modified, or synthetic biomolecule, such as an antibody, protein, enzyme, DNA, RNA, peptide, whole cell, etc., or chemical group that has selectivity for a target analyte. Alternatively, the reactive group 34 itself can be the chem/bio recognition group 37. Coupling or crosslinking chemistries include, but are not limited to, free amine groups on the surface of the chem/bio recognition molecule coupled to a bound aryl-diazonium that has an activating carboxyl functional group on the phenyl ring. Alternatively, molecule that has an amine functional group. Additional chemistries include, but are not limited to, boronic acid groups binding to saccharides, maleimide groups binding to thiols, biotin groups binding to streptavidin, etc. In practice, a plurality of such electroactive bound diazonium molecules form a chem/bio selective layer on the surface of the electrode, enabling electrochemical detection of the target analyte(s). The surface density of the bound diazonium molecules can be controlled by the electrodeposition protocol.

Figure 3:
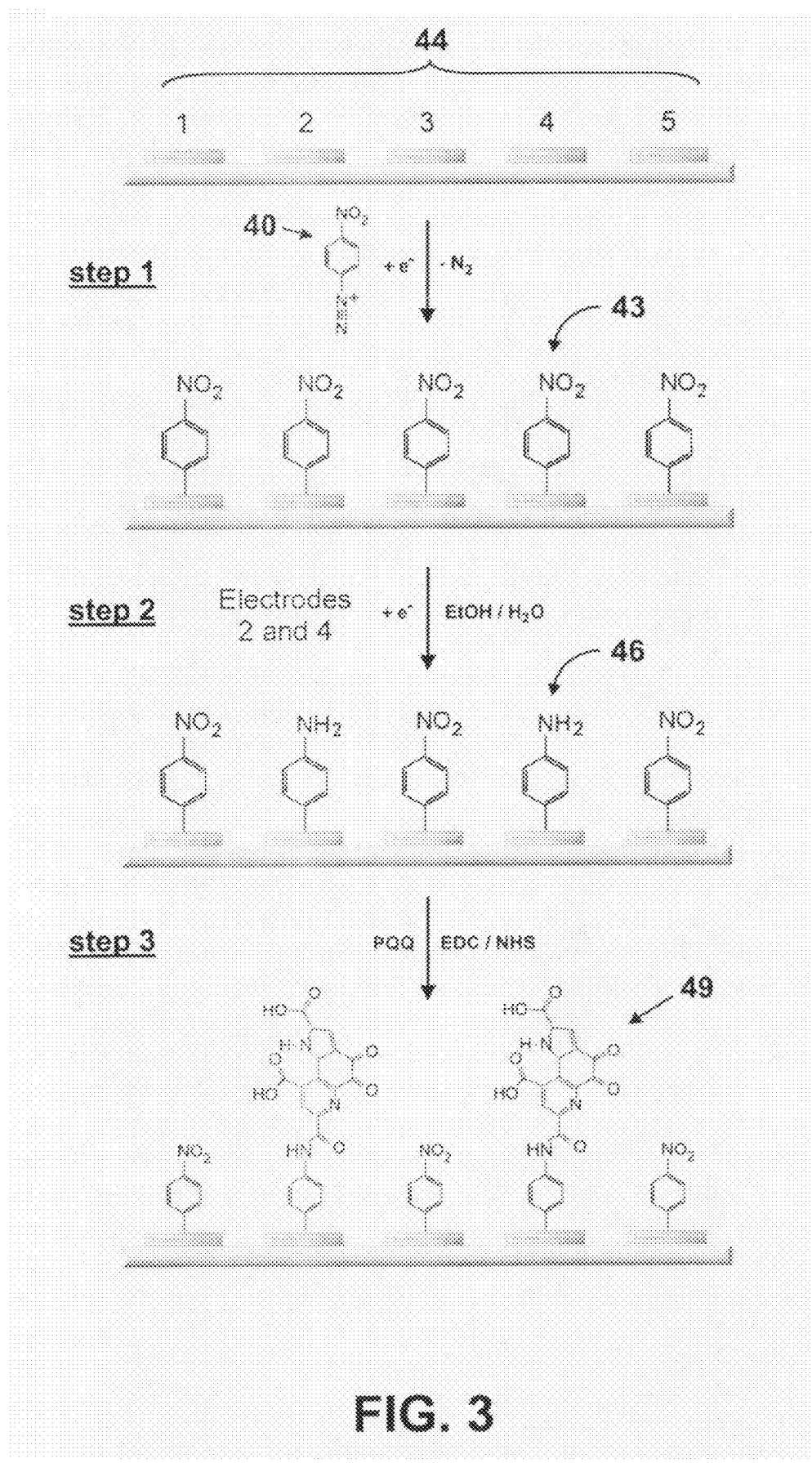
FIG. 3 shows a schematic illustration of the electro-addressable functionalization of selected electrodes of an electrode array, wherein nitrophenyl diazonium is electrodeposited onto the electrodes of the array, the assembled diazonium on the addressed electrodes is activated via bias-driven reduction of nitrophenyl to aminophenyl groups under protic conditions, and the activated electrodes are functionalized with PQQ via carbodiimide catalyzed amide bond formation.

In FIG. 3 is shown an example of the method of the present invention, wherein diazonium chemistry was used for the selective functionalization of electrodes of an array with controlled surface density of the NADH oxidant, PQQ. The nicotinamide redox co-factor, $NAD^+$, is essential for the biocatalytic activation of over 300 dehydrogenase enzymes (e.g., lactate dehydrogenase, alcohol dehydrogenase, glucose dehydrogenase). See E. Simon and P. N. Bartlett, *Biomolecular Films Design, Function and Applications*, Rusling, J. F., Ed., Marcel Dekker New York, pp 499-544 (2003). Detection of the biocatalytically produced NADH has been used to measure enzymatic activity for respective substrate molecules (e.g., lactate, malate, and ethanol) in which the NADH molecule serves to shuttle electrons from enzyme to anode. See A. Bardea et al., *J. Am. Chem. Soc.* 119, 9114 (1997); I. Willner and A. Riklin, *Anal. Chem.* 66, 1535 (1994); P. Ramesh et al., *J. Electroanal. Chem.* 528, 82 (2002); G. T. R. Palmore et al., *J. Electroanal. Chem.* 443, 155 (1998); and I. Willner et al., *Bioelectroch. Bioener.* 44, 209 (1998). The exemplary method comprises the electro-addressable activation of diazonium-modified gold electrodes for selective functionalization of the array. The electrodes were modified with 4-nitrophenyl diazonium. Addressed electroreduction of nitro groups to amines allowed selective immobilization of pyrroloquinoline quinone (PQQ). The activated electrodes showed great efficacy towards the oxidation of β-nicotinamide adenine dinucleotide (NADH). Electrodes that were not electro-reduced to the amine were not functionalized with PQQ, retaining deactivated nitro functionality, and were protected from non-specific absorption and mild chemical reactions.

At step 1, 4-nitrophenyl diazonium molecules 40 were electrodeposited onto an array 44 of clean gold electrodes (1, 2, 3, 4, and 5) via bias-assisted assembly. The 500-μm diameter gold disk arrayed electrodes (1, 2, 3, 4, and 5) were prepared via thermal evaporation of a 200 Å Ti adhesion layer followed by 2000 Å of Au onto a Pyrex wafer. The Au electrodes were piranha cleaned (5:3 conc. sulfuric acid: 30% $H_2O_2$) for 5 min, washed with nanopure water, and dried under a stream of nitrogen. The nitrophenyl diazonium salt (4-nitrophenyl tetrafluoroborate) 40 was synthesized according to the method of Doyle. See M. P. Doyle and J. W. Bryker, *J. Org. Chem.* 44, 1572 (1979). The aryl-diazonium salt 40 has a nitro group $NO_2$ that it not reactive (deactivated) towards carbodiimide coupling chemistry, at the para position of the phenyl ring. Nitrophenyl diazonium thin films were assembled onto the clean gold electrodes using chronoamperometry, linear sweep, or cyclic sweep methods in a solution of 1 mM nitrophenyl diazonium and 0.1 M tetrabutylammonium tetrafluoroborate ($Bu_4NBF_4$) in acetonitrile (ACN). After electrodeposition the electrodes were briefly rinsed with ACN, followed by an ethanol rinse and a 15 second sonication in ethanol to remove any adsorbed nitrophenyl diazonium. After sonication the electrodes were again rinsed in ethanol and dried under a stream of nitrogen to provide the covalently bound nitrophenyl diazonium electrodes 43.

Figure 4:
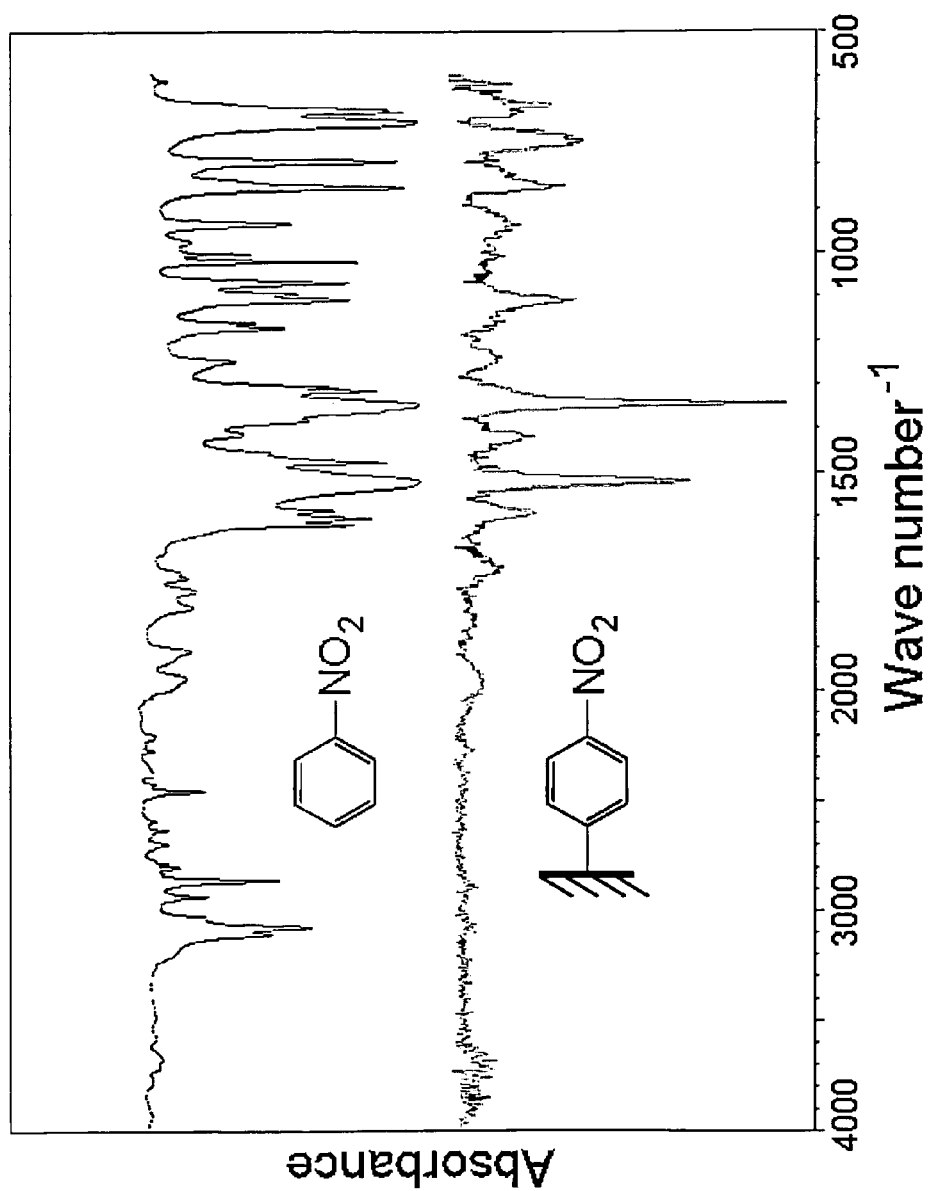
FIG. 4 shows a graph of grazing angle FTIR spectrum of nitrobenzene and a gold electrode prepared from a 10 CV electrodeposition of nitrophenyl diazonium.

Grazing angle FTIR was used to verify assembly of the nitrophenyl diazonium molecules on the gold electrodes and retention of the nitro functional group. In FIG. 4 are shown the grazing incidence FTIR spectra of nitrobenzene and a 1-cm diameter gold electrode prepared from a 10-cycle cyclic voltammetry (CV) electrodeposition of 4-nitrophenyl diazonium. The two sharp peaks at 1528 $cm^{-1}$ and 1352 $cm^{-1}$ are common to both the nitrobenzene and the 4-nitrophenyl diazonium assembled electrode spectra. These absorption stretches are characteristic of the asymmetric and symmetric stretch modes, respectively, of the nitro group and provide strong evidence that the nitrophenyl diazonium assembled onto the gold substrate with the nitro functional group intact and unreduced. A control electrode immersed in nitrophenyl diazonium assembly solution for 3 minutes, without bias/CV, followed by brief sonication and rinsing did not produce significant absorption stretches.

Control Over Functionalized Surface Density and Electron Transfer Kinetics Using Diazonium Electrodeposition Protocol The surface density of the bound nitrophenyl diazonium molecules can be controlled by the electrodeposition protocol. Four different protocols were used for electrodeposition assembly: 1) 1 minute duration chronoamperometric (CA) step to −1 V; 2) linear sweep (LS) from 0 to −1 V at 100 mV/s; 3) CV from 0 to −1 to 0 V at 100 mV/s; and 4) 2 CVs from 0 to −1 to 0 V at 100 mV/s. In Table 1 are shown the average diazonium film thicknesses for electrodes prepared from these different protocols, as measured by ellipsometry. Potential sweep protocols (LS and CV) produced the thickest films. Further, electrodes prepared from increased number of CV sweeps showed increased film thickness per longer deposition times. However, variability in film thickness uniformity also increased with increasing number of sweeps.

| Electro-deposition Method | Film Thickness (Å) | $\Gamma$ (mol $NO_2$/cm$^2$) | $\Gamma$ (mol PQQ/cm$^2$) | $k_s$ (s$^{-1}$) |
|---|---|---|---|---|
| 1 min CA | 4.2 ± 0.82 | 0.99 × 10$^{-12}$ | 0.91 × 10$^{-12}$ | 9.5 ± 0.6 |
| 1 LS | 5.9 ± 0.54 | 7.6 × 10$^{-12}$ | 1.3 × 10$^{-12}$ | 7.3 ± 0.5 |
| 1 CV | 9.3 ± 1.6 | 11 × 10$^{-12}$ | 1.6 × 10$^{-12}$ | 5.8 ± 0.6 |
| 2 CVs | 10.4 ± 2.2 | 20 × 10$^{-12}$ | 2.0 × 10$^{-12}$ | 4.7 ± 0.4 |

Returning now to FIG. 3, at step 2, selected 4-nitrophenyl-modified electrodes were activated towards carbodiimide chemistry by electro-reduction of the unreactive nitrophenyl groups $NO_2$, in protic medium, to aminophenyl groups $NH_2$, which are active towards carbodiimide chemistry. Conversion of the selected nitrophenyl-modified electrodes 43 to aminophenyl-modified electrodes 46 was achieved by cyclic voltammetry from −300 to −1300 mV in deoxygenated (argon sparge) ethanol:water (1:9) solution with 0.1 M KCl as electrolyte.

Figure 5:
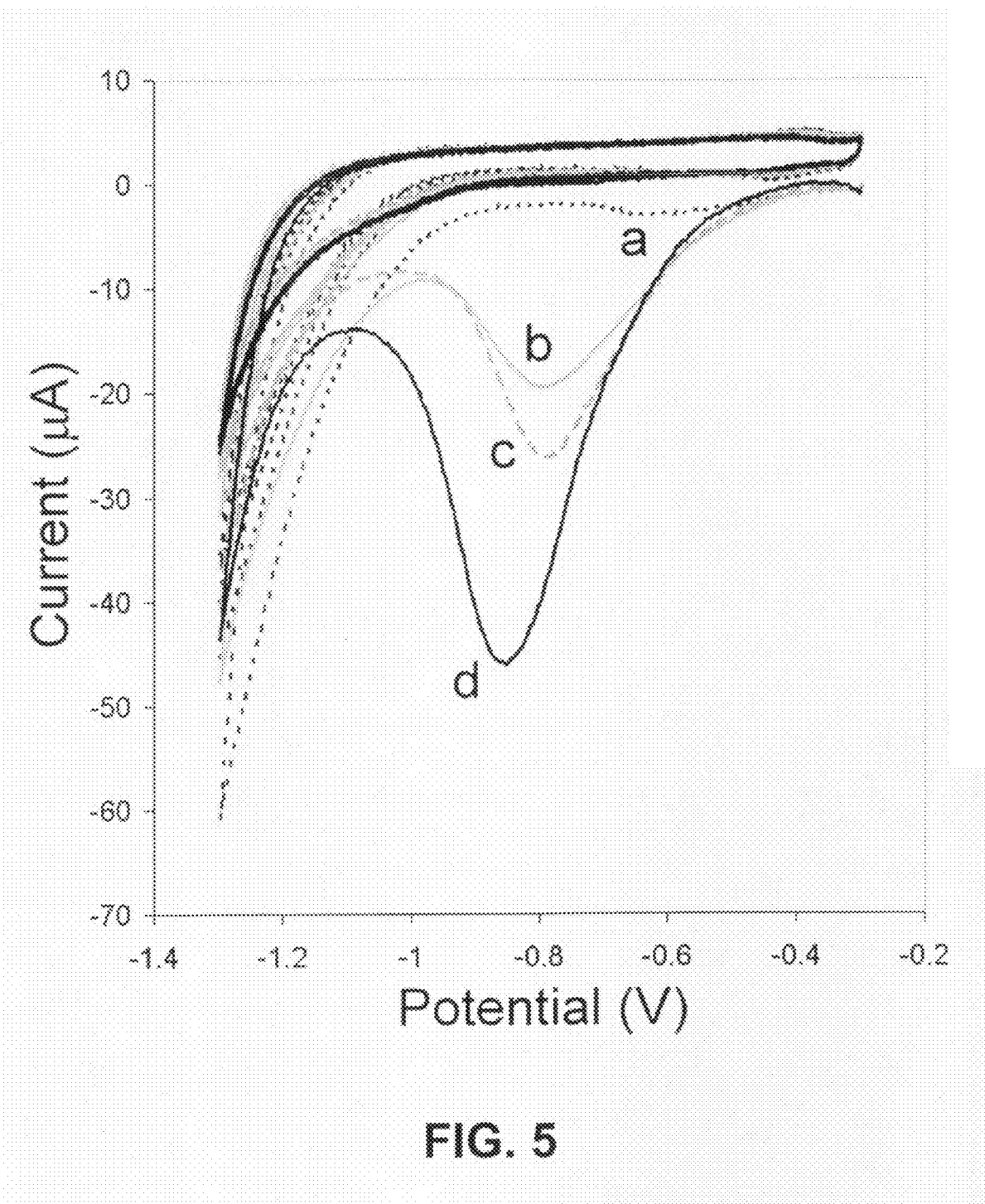
FIG. 5 shows cyclic voltammograms of nitrophenyl modified gold electrodes in a 0.1 M KCl, ethanol:water (1:9) solution, v=100 mV/s, under argon. Electrodeposition method for nitrophenyl modification: 1 min CA (a), 1 LS (b), 1 CV (c) and 2 CVs (d).

In FIG. 5 are shown cyclic voltammograms of nitrophenyl-modified gold electrodes in a 0.1 M KCl, ethanol:water (1:9) solution, v=100 mV/s, under argon. The electrodeposition methods for nitrophenyl modification were: 1 min CA (a), 1 LS (b), 1 CV (c), and 2 CVs (d). The first reductive sweep in aqueous solution produces a sharp wave corresponding to the six electron reduction reaction of nitrophenyl to aminophenyl. This peak was not observed in subsequent sweeps, indicating complete conversion of all electrically accessible nitro groups. The area of the reduction peak corresponds to the total charge transferred during the reaction, and hence, the number of electrically accessible nitro groups on the electrode surface. In Table 1 is shown the surface concentration, $\Gamma$, of accessible nitro groups. The greatest surface concentration of $NO_2$ corresponds to the electrode assembled with 2 CVs and is followed by electrodes prepared from 1 CV, 1 LS, and 1 min CA, respectively. This trend agrees with the average film thickness data obtained from ellipsometry. The greater rate of increase in $NO_2$ group surface concentration, compared to the increase in total film thickness, indicates an increasing density of the thin film during deposition. The potential at which the reduction wave occurs also shifts in the negative direction for electrodes assembled with increased film thickness. The higher overpotential required for the reduction reaction is a manifestation of the higher resistance to electron transfer due to the increasing film thickness. This trend also correlated well with film thickness data obtained from ellipsometry. After the initial nitro reduction wave, a small reversible wave was observed centered near −400 mV. This reaction is likely the reoxidation/reduction of 4-hydroxylamino phenyl groups which are intermediates of the nitro to amine reduction reaction. See M. Delmar et al., Carbon 35, 801 (1997).

Returning now to FIG. 3, at step 3, following reduction of the nitrophenyl to aminophenyl groups, the activated electrodes were functionalized with PQQ via carbodiimide chemistry which forms amide bonds between primary amines and carboxylic acid groups. After activation, the electrodes were rinsed in water, dried under a stream of nitrogen, and immersed into a solution of 10 mM 1-ethyl-3-[3-dimethylaminopropyl]carbodiimide hydrochloride (EDC), 1 mM N-hydroxysuccinimide (NHS), and 1 mM pyrroloquinoline quinone (PQQ), in 10 mM 2-[4-(2-Hydroxyethyl)-1-piperazine]ethanesulfonic acid (HEPES) buffer, pH 7.5. After two hours of treatment in this solution, the electrodes were again rinsed in water and dried with nitrogen. When treated with PQQ in the presence of EDC and NHS, an amide bond is formed between the amino activated electrodes and carboxyl groups on PQQ to provide the electroactive PQQ modified phenyl diazonium surface 49 on the selected electrodes 2 and 4. The electroactive electrodes 49 have selectivity for the analyte NADH.

Figure 6:
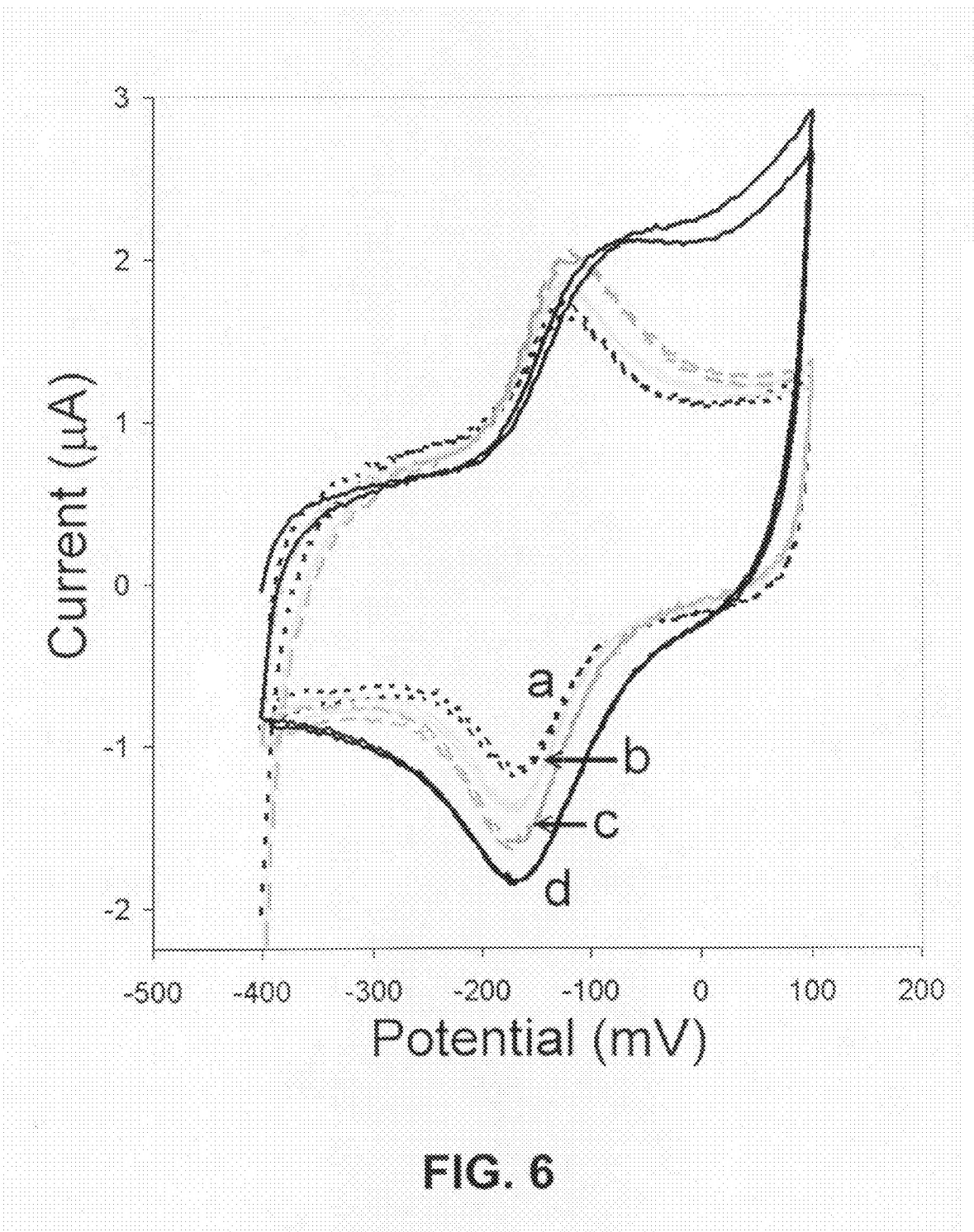
FIG. 6 shows cyclic voltammograms of PQQ functionalized gold electrodes in 0.1 M Tris-HCl buffer, pH 7.4, v=200 mV/s, under argon. Electrodeposition method for nitrophenyl modification: 1 min CA (a), 1 LS (b), 1 CV (c) and 2 CVs (d).

In FIG. 6 are shown cyclic voltammograms of PQQ-functionalized gold electrodes in 0.1 M tris-HCl buffer, pH 7.4, v=200 mV/s, under argon. The electrodeposition methods for nitrophenyl modification were: 1 min CA (a), 1 LS (b), 1 CV (c), and 2 CVs (d). A quasi-reversible redox wave with formal potential, $E^{0'}$=−144 mV was observed. This formal potential is similar to that reported for PQQ immobilized to a gold electrode via a self assembling monolayer of cystamine, $E^{0'}$=−160 (vs. Ag/AgCl) at pH 7.0. See E. Katz et al., J. Electroanal. Chem. 367, 59 (1994). Further control experiments with nitrophenyl- and aminophenyl-modified electrodes treated with PQQ solution in the absence of EDC and NHS failed to generate redox waves in the window of interest. Peak separation, $\Delta E_p$, at v=25 mV/s, was 18 mV. This $\Delta E_p$ is greater than the theoretical 0 mV expected for reversible surface confined species, but less than the 30 mV expected for two electron transfer diffusion based electrochemistry. This low $\Delta E_p$, and the linear dependence of peak currents on potential scan rates obtained for the PQQ modified electrodes, are characteristic of a surface confined electroactive species.

In Table 1 is shown the surface concentration of immobilized PQQ, calculated from the area of the reduction waves. A strong correlation is again observed between diazonium film thickness, $NO_2$ surface concentration, and the surface concentration of PQQ. Electrodes prepared from 1 min CA showed nearly all converted $NO_2$ groups reacted to immobilize PQQ. This suggests that the nitrophenyl film formed a monolayer with uniform density such that immobilized PQQ did not sterically hinder unconjugated PQQ from binding to nearby free amine binding sites. In contrast, only 17% of converted $NO_2$ groups reacted to bind PQQ from the 1 LS deposition. Explanations for this observation include steric hindrance of the large PQQ molecules blocking access to free surface amino groups. Additionally, as increasing layers of nitrophenyl are deposited, more $NO_2$ groups are converted to amines. However, converted amine groups on layers closer to the electrode are not accessible to the reaction solution and are not conjugated. This same trend is followed for electrodes prepared from 1 and 2 CV depositions. The immobilized concentration and density of $NO_2$ groups increases, while only non-sterically hindered groups on the outermost layer accessible to the solution are conjugated.

The heterogeneous electron transfer coefficient, $k_s$, for electrodes prepared from the four electrodeposition protocols were also calculated and reported in Table 1. As expected, lower $k_s$ values were obtained as diazonium film thickness increased indicating a trade-off between PQQ surface coverage and facile electron transfer between PQQ and the electrode. A product of this trade-off may be the current response obtained from the PQQ modified electrode prepared from 2 CVs, shown in FIG. 6(d). Although the reduction wave closely follows the increasing PQQ density trend of the other electrodes, the oxidation wave has broadened and shifted significantly more positive when compared to the oxidation wave obtained from the other 3 assembly protocols. This result was highly reproducible and may be due either to crossing a threshold for increased resistance to oxidative electron transfer at average film thicknesses greater than approximately 10 Å or electrostatic interactions with nearby PQQ groups as the conjugated surface density increases.

Electrochemical Catalytic Biochemical Detection

Figure 7:
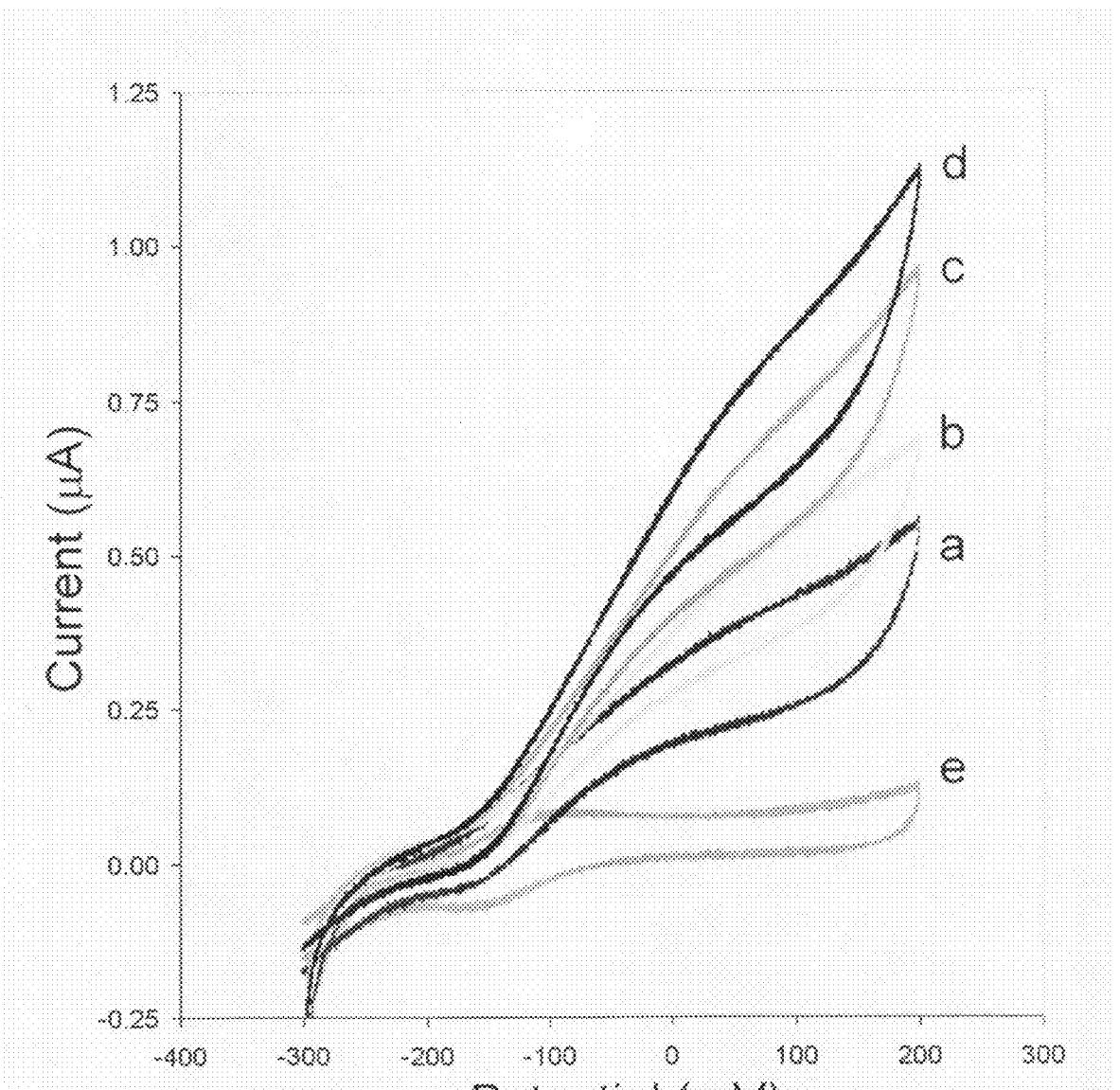
FIG. 7 shows cyclic voltammograms of catalytic NADH oxidation at PQQ functionalized gold electrodes in 10 mM NADH, 20 mM $Ca^{2+}$, 0.1 M Tris-HCl buffer, pH 7.4, v=20 mV/s. Electrodeposition method for nitrophenyl modification: 1 min CA (a), 1 LS (b), 1 CV (c) and 2 CVs (d). No catalytic oxidative current was observed from a PQQ functionalized electrode prepared from a 2 CV nitrophenyl diazonium electrodeposition in the absence of NADH (e).

In FIG. 7 are shown cyclic voltammograms of the catalytic β-nicotinamide adenine dinucleotide (NADH) oxidation at PQQ functionalized gold electrodes in 10 mM NADH, 20 mM $Ca^{2+}$, 0.1 M Tris-HCl buffer, pH 7.4, v=20 mV/s. The electrodeposition methods for nitrophenyl modification were: 1 min CA (a), 1 LS (b), 1 CV (c), and 2 CVs (d). The cyclic voltammograms showed an enhanced oxidative wave and no reduction wave characteristic of catalytic electrochemical oxidation. It has been reported that the presence of $Ca^{2+}$ enhances the catalytic current obtained from NADH oxidation via PQQ. See E. Katz et al., *J. Electroanal. Chem.* 373, 189 (1994). The overall magnitude of the current response in relation to the four different immobilization strategies was directly proportional to the surface coverage of the immobilized PQQ. This suggests that under the relatively small time frame of these experiments (v=20 mV/s) that increasing the number of catalytic sites, or immobilized PQQ, has a greater effect on current output than the decrease in $k_s$ obtained from thicker films. No catalytic oxidative current was observed from a PQQ functionalized electrode prepared from a 2 CV nitrophenyl diazonium electrodeposition in the absence of NADH (e).

Electro-Addressable Selective Functionalization

Figure 8:
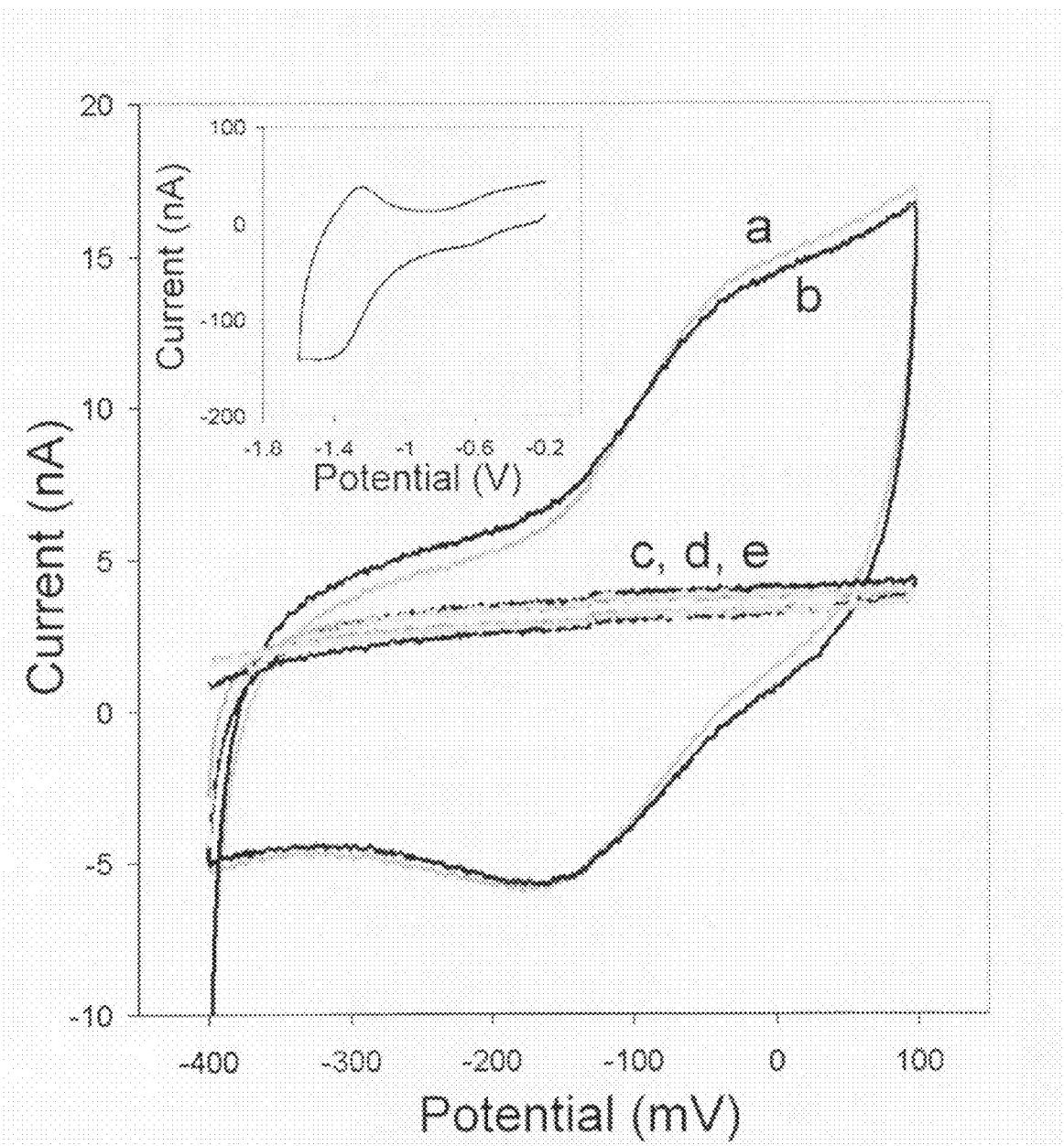
FIG. 8 shows the electro-addressable activation of two electrodes in a five element array for selective functionalization with PQQ. Cyclic voltammograms of activated working electrodes (a) and (b) and inactive working electrodes (c), (d), and (e) after PQQ/EDC/NHS treatment in 0.1 M Tris-HCl buffer, pH 7.4, v=25 mV/s. Inset is a representative cyclic voltammogram of an inactive ($NO_2$) working electrode in 0.1 M $Bu_4NBF_4$ in ACN, under argon.

FIG. 8 shows the electro-addressable activation of two electrodes in a five element array for selective functionalization with PQQ. Shown are cyclic voltammograms (a) and (b) of activated working electrodes 2 and 4, respectively, and cyclic voltammograms (c), (d), and (e) of inactive working electrodes 1, 3, and 5, respectively, after PQQ/EDC/NHS treatment in 0.1 M Tris-HCl buffer, pH 7.4, v=25 mV/s. The inset is a representative cyclic voltammogram of an unreactive ($NO_2$) working electrode in 0.1 M $Bu_4NBF_4$ in ACN, under argon. To prepare the array, the five closely spaced 500 μm diameter gold electrodes were each treated with a 1 CV nitrophenyl diazonium electrodeposition. Following diazonium deposition, the array was immersed in aqueous solution and the two electrodes 2 and 4 were electrochemically activated by reduction of the nitrophenyl to aminophenyl. The array was subsequently treated in PQQ carbodiimide solution. The activated electrodes 2 and 4 showed the quasi-reversible waves for immobilized PQQ while the inactive electrodes 1, 3, and 5 showed no redox activity in the potential window investigated. In non-aqueous conditions, the inactivated electrodes also showed redox waves typical of nitro group electrochemistry centered near −1.3 V, as shown in the inset of FIG. 8. This demonstrates the novelty of electro-addressable selective functionalization of a single electrode in an electrode array in which inactive electrodes are protected from mild chemical reactions, non-specific absorption, and maintain the nitro functionality while activated electrodes are readily functionalized using classical amine coupling chemistry. Also possible is the subsequent modification of arrayed electrodes with different chem/bio recognition groups by stepwise chemical and/or electrochemical activation of individual electrodes.

Figure 9:
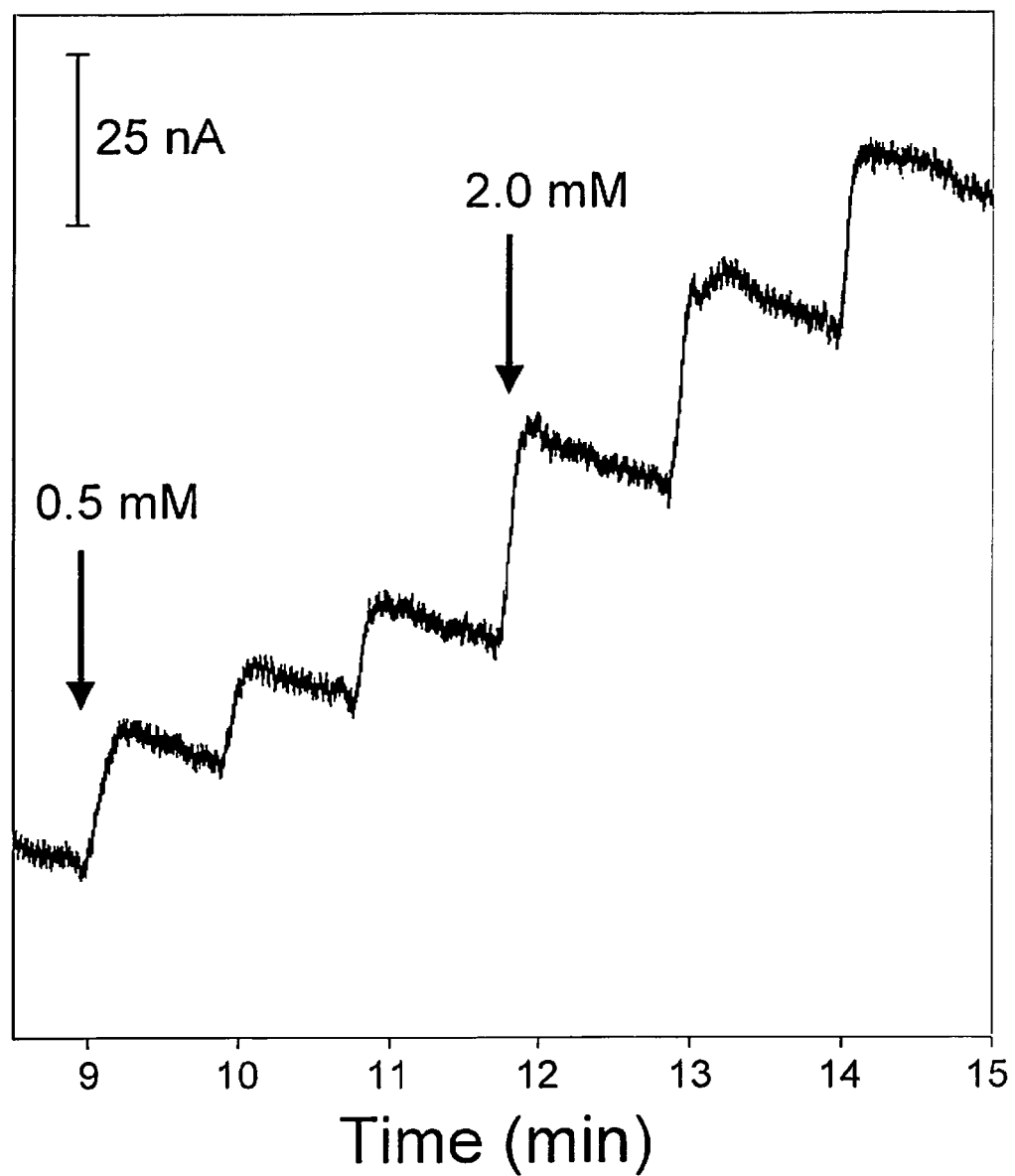
FIG. 9 shows a graph of chronoamperometric response of a PQQ functionalized electrode prepared from a 2 CV nitrophenyl diazonium electrodeposition at a potential of 100 mV in 20 mM $Ca^{2+}$, 0.1 M Tris-HCl buffer, pH 7.4, with stirring, and three subsequent additions each of 0.5 mM, and 2.0 mM NADH.
Figure 10:
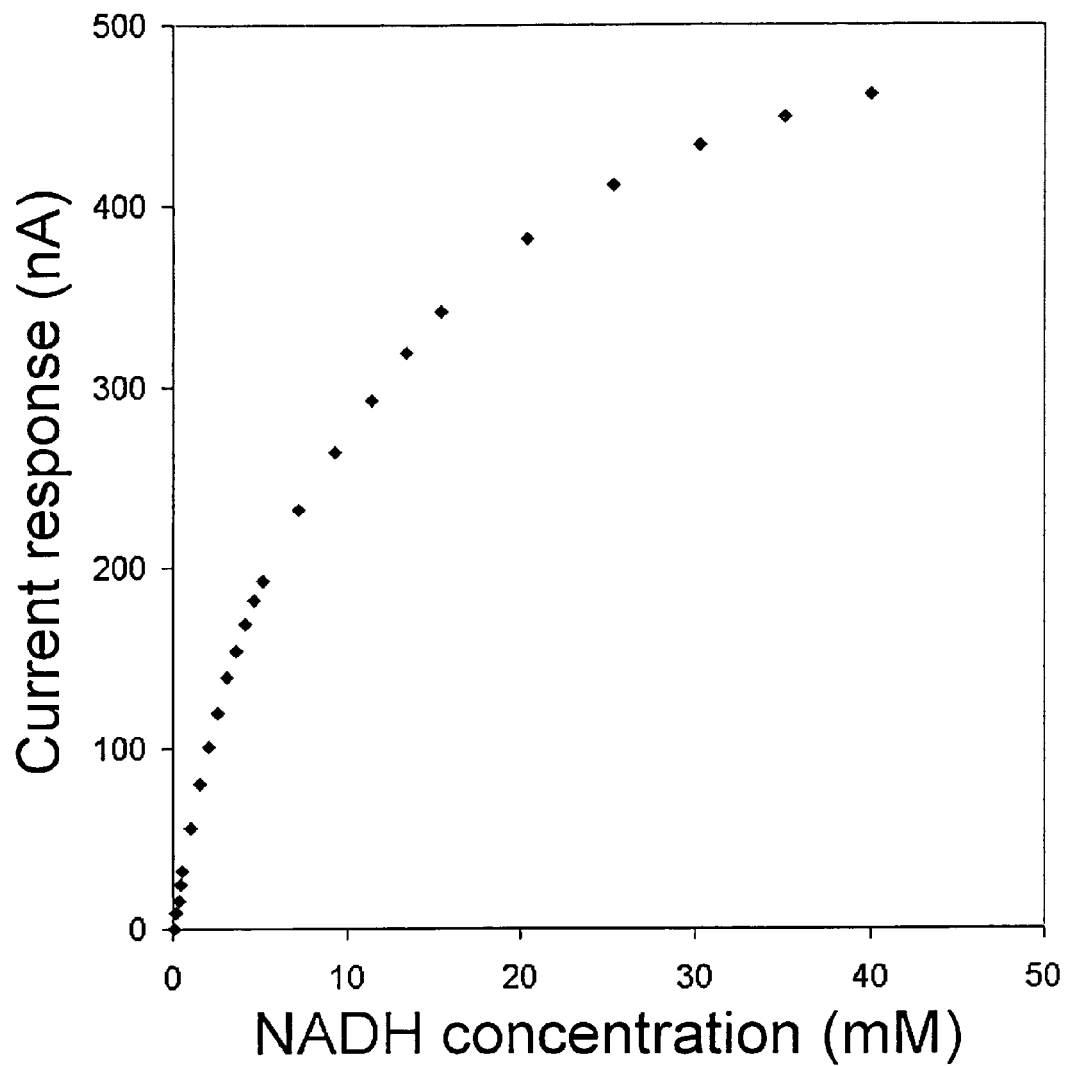
FIG. 10 shows a graph of current response of a PQQ functionalized electrode prepared from a 2 CV nitrophenyl diazonium electrodeposition to NADH concentration.

Amperometric detection of NADH was performed using a PQQ functionalized electrode prepared from a 2 CV electrodeposition held at a constant potential of 100 mV in a stirred solution. FIG. 9 shows a graph of chronoamperometric response of a PQQ functionalized electrode prepared from a 2 CV nitrophenyl diazonium electrodeposition at a potential of 100 mV in 20 mM $Ca^{2+}$, 0.1 M Tris-HCl buffer, pH 7.4, with stirring, and three subsequent additions each of 0.5 mM, and 2.0 mM NADH. A fast current response is obtained reaching a steady state value in 5-10 seconds. The change in current upon NADH injection was linear with respect to NADH concentration up to 10 mM with saturation occurring at concentrations near 30 mM, as shown in FIG. 10. The detection limit was approximately 100 μM NADH and is comparable to that reported for other PQQ based NADH detection systems.

Preparation of a Cell-Base Biosensor Via Chemical or Electrochemical Deprotection of a Reactive Binding Molecule Recently there has been much interest in the development of cell arrays for such areas as drug screening, gene expression profiling, stem-cell differentiation, understanding higher-level organization of tissues and organisms, and other developing fields involving biology systems' functions. Cell based arrays have the potential to lead to a new generation of powerful biosensors as living cells contain specific biological and chemical receptors with processes that respond to minute concentrations of molecules. The ability to easily control the spatial organization and interactions between populations of cells would also prove valuable for research involving cell-cell or host-pathogen interactions and cell signaling pathways.

Some common cell attachment and detachment protocols utilize native poly- and oligo-saccharides that are present in the outer cellular wall or membrane and can bind to many sugar-specific proteins and antibodies. So called artificial lectins, such as boronic acid, can form esters with diols to generate five- or six-membered cyclic complexes that can also be exploited to capture cells. See A. E. Ivanov et al., *Chem. Eur. J.* 12, 7204 (2006). The boronic acid-saccharide interaction is particularly attractive for a number of reasons. In the physiological pH range of 6.8-7.5, boronic acid provides a stable boronate anion that reacts with 1,2- or 1,3-diols forming reversible complexes. The formation of this complex is highly dependant upon the nature of a given saccharide and has been exploited in numerous applications. See S. Liu and B. Miller, *Electrochem. Comm.* 7, 1232 (2005).

Figure 11:
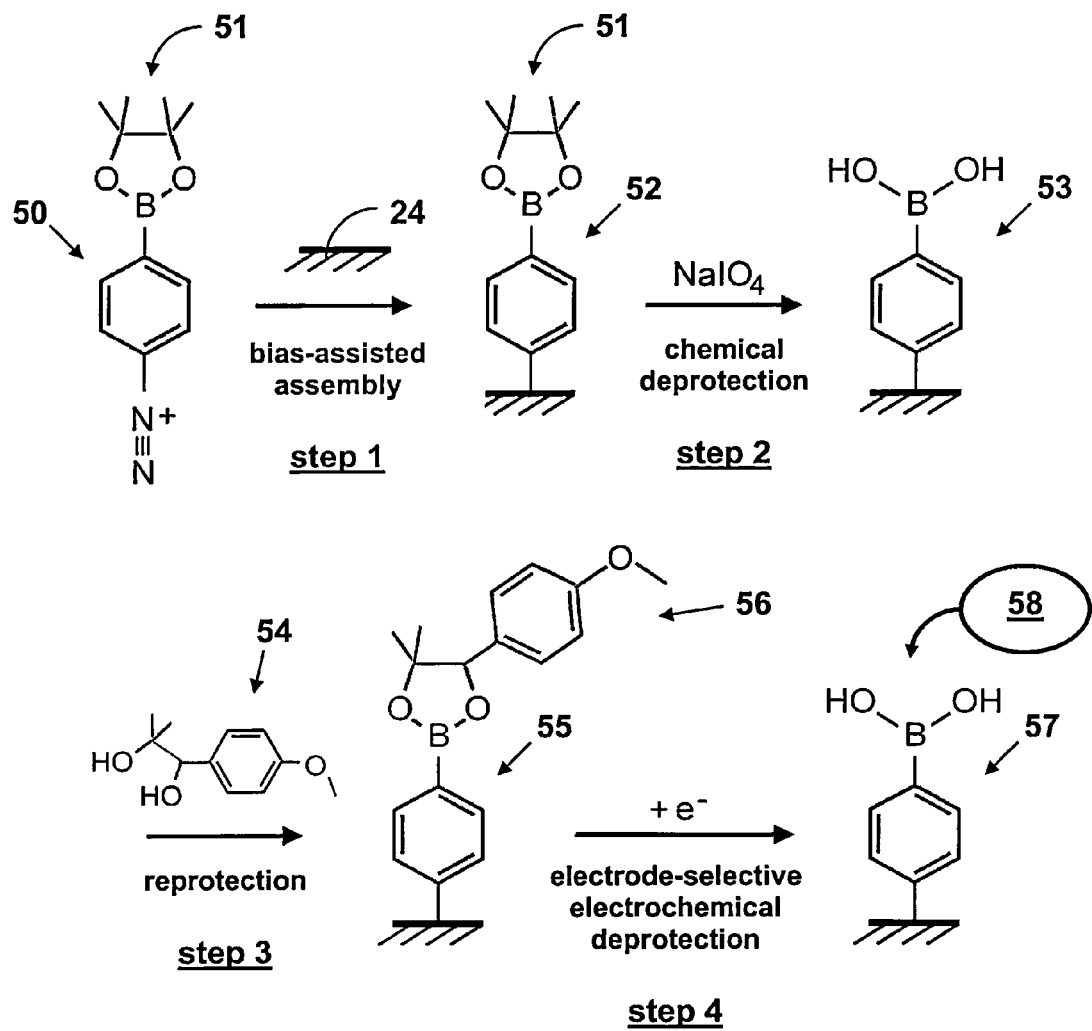
FIG. 11 shows a schematic illustration of phenyl boronic acid functionalization of an electrode array, wherein phenyl boronic acid diazonium salts are used to activate individual electrodes of the electrode array for facile and reversible cell immobilization.

In FIG. 11 is shown another example of the method of the present invention, wherein phenyl boronic acid diazonium salts are used to activate individual electrodes of an electrode array for facile and reversible cell immobilization (e.g., yeast and macrophage). Phenyl boronic acid pinacol ester diazonium 50 was synthesized with a pinacol ester blocking group 51 on the boronic acid. To synthesize synthesis the diazonium salt, nitrosonium tetrafluoroborate ($NOBF_4$, 0.315 g, 2.69 mmoles) was dissolved in anhydrous acetonitrile (ACN, 5 mL) under nitrogen and then cooled to −40° C. The 4-aminophenylboronic acid pinacol ester (0.53 g, 2.42 mmole) was dissolved in 12 mL of ACN under nitrogen. The amine solution was added slowly by cannula to the stirred −40° C. solution of the NOBF$_4$. The resulting solution was stirred 1 hour at −40° C. and then allowed to warm to 0° C. and then stirred an additional 10 minutes. This solution was cannulated into 800 mL of rapidly stirred cold diethyl ether in air. The resulting precipitate was collected on a buchner funnel and dried under vacuum. This synthesis provided an 83% yield (0.64 g, 2.0 mmoles) of 4-(4,4,5,5-tetramethyl-1,3,2-dioxaborolan-2-yl)benzenediazonium.

An array of individual electrodes 24 was prepared for electrodeposition of the diazonium salt 50. 500-μm diameter gold disk arrayed electrodes, spaced 1.5 mm apart, and 5 mm diameter gold disk electrodes were prepared via thermal evaporation of a 200 Å Ti adhesion layer followed by 2000 Å of Au onto a Pyrex wafer. The gold electrodes were cleaned immediately before use with freshly prepared piranha (5:3 conc. sulfuric acid: 30% H$_2$O$_2$) for 5 min, washed with nanopure water, and dried under a stream of nitrogen.

At step 1, phenyl boronic acid pinacol ester diazonium 50 was electrodeposited onto the electrode 24, forming a pinacol ester blocked phenylborate modified electrode surface 52. For this example, the phenyl boronic acid pinacol ester thin films were assembled onto the clean gold electrodes using cyclic voltammetry in a solution of 1 mM phenyl boronic acid pinacol ester diazonium and 0.1 M tetrabutylammonium tetrafluoroborate (Bu$_4$NBF$_4$) in ACN. After electrodeposition, the electrodes were briefly rinsed with ACN, followed by a rinse with ethanol and a 15 second sonication in ethanol to remove any absorbed phenyl boronic acid pinacol ester diazonium. After sonication the electrodes were again rinsed in ethanol and dried under a stream of nitrogen.

At step 2, the pinacol ester blocking group 51 was chemically deprotected with an oxidant, sodium periodate (NaIO$_4$), forming a phenyl boronic acid surface 53. For this example, the protected electrodes 52 were treated with 100 μl of 50 mM NaIO$_4$ (4:1 water:THF) for 30 min to remove the pinacol blocking ester, rinsed with water and dried under nitrogen.

At step 3, the deprotected electrodes 53 were reblocked with a MPMP-diol reprotection unit 54. For this example, 2-(4-methoxyphenyl)ethyl acetate was allowed to react with excess methylmagnesium bromide in tetrahydrofuran (THF) to provide after aqueous workup 1-(4-methoxyphenyl)-2-methylpropan-2-ol. This was brominated with NBS in carbon tetrachloride at reflux for 12 hours. Hydroylsis of the resulting 1-bromo-1-(4-methoxyphenyl)-2-methylpropan-2-ol was performed with freshly prepared silver carbonate in aqueous acetone. The resulting 1-(4-methoxy-phenyl)-2-methyl-propane-1,2-diol (MPMP-diol) was identical spectroscopically with that reported in the literature. See J. Yan et al., *Tetrahed. Lett.* 46, 8503 (2005). The unblocked electrode was then treated with 100 μl of 10 mM MPMP-diol reprotection unit in anhydrous toluene for 30 min to provide the reprotected electrode 55. The reprotected electrodes 55 comprised para-methoxybenzyl groups 56 that provide a protecting group that can be removed through oxidation. The MPMP-diol protecting group has been previously used to protect borate esters. See J. Yan et al., *Tetrahed. Lett.* 46, 8503 (2005).

At step 4, electro-addressable deprotection was again used to provide a phenyl boronic acid surface 57, but only at the electrically bias electrodes. For this example, the second deprotection was performed electrochemically by applying a +0.6 V potential to a selected electrode in 0.1 M phosphate buffer, pH 7.4, for 60 sec followed by rinsing with water and drying under nitrogen. The electrochemical deprotection oxidizes the MPMP-diol to 2-hydroxy-1-(4-methoxyphenyl)-2-methylpropan-1-one which cannot bind effectively to the boric acid thereby shifting the equilibrium to the free boronic acid. See J. Yan et al., *Tetrahed. Lett.* 46, 8503 (2005). The boronic acid surface is active towards binding of saccharide groups. This interaction can be used to immobilize sugars, glycoproteins, or whole cells 58 onto the selected electrodes that have specific biological or chemical receptors to detect a target analyte.

Figure 12:
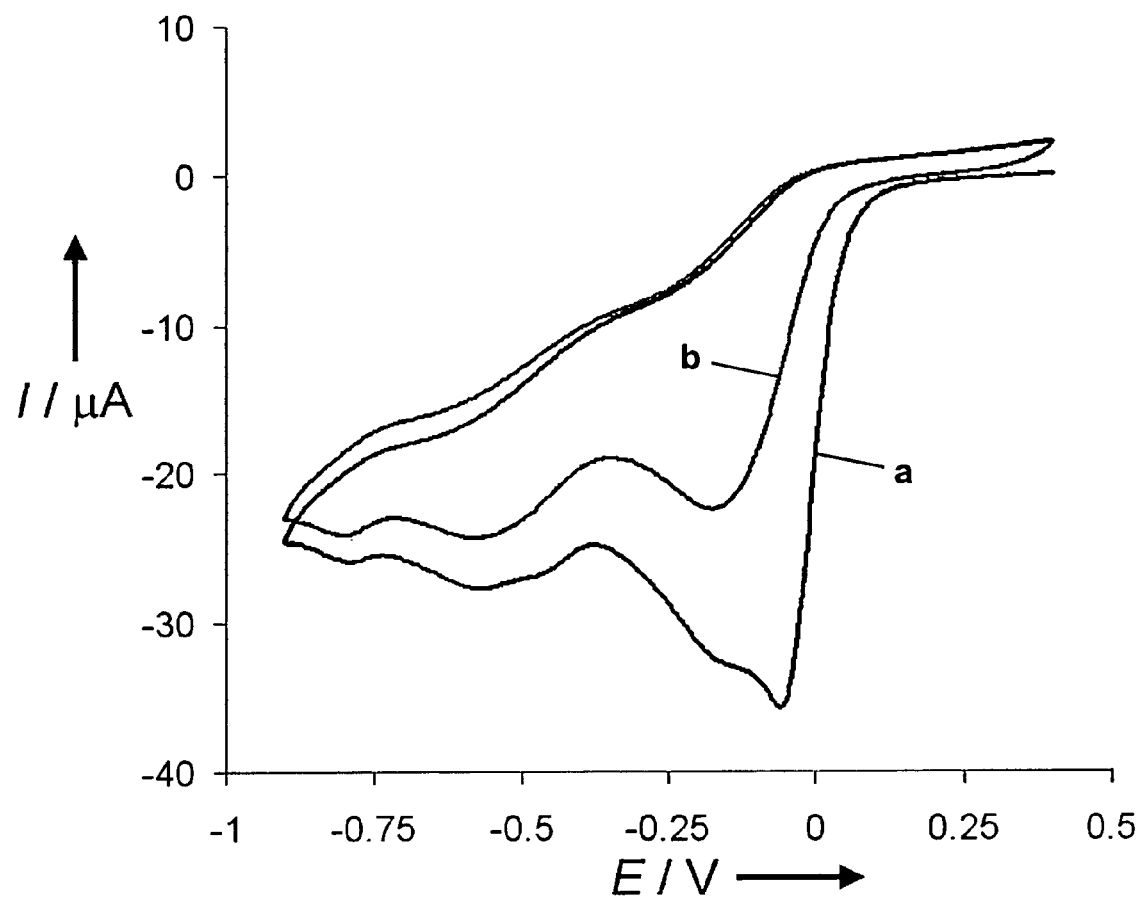
FIG. 12 shows cyclic voltammograms of 1 mM phenyl boronic acid pinacol ester diazonium on a gold disk electrode with 0.1 M $Bu_4NBF_4$ in ACN, v=100 mV $s^{-1}$.

In FIG. 12 are shown cyclic voltammograms from the first and second cycles of 1 mM phenyl boronic acid pinacol ester diazonium in acetonitrile electrodeposition onto a gold disk electrode (i.e., step 1). The first cycle (a) exhibits a well-defined, reproducible, and irreversible reduction peak at −0.089V vs. Ag/AgNO$_3$ with a small shoulder at about −0.14V. This first sharp peak is absent on subsequent scans, as shown in the second scan in (b), and is attributed to the electroreduction of the diazonium functional group. This leads to the elimination of di nitrogen and the production of an aryl radical that can react with the electrode surface forming a covalent bond between the aryl group and the electrode.

Figure 13:
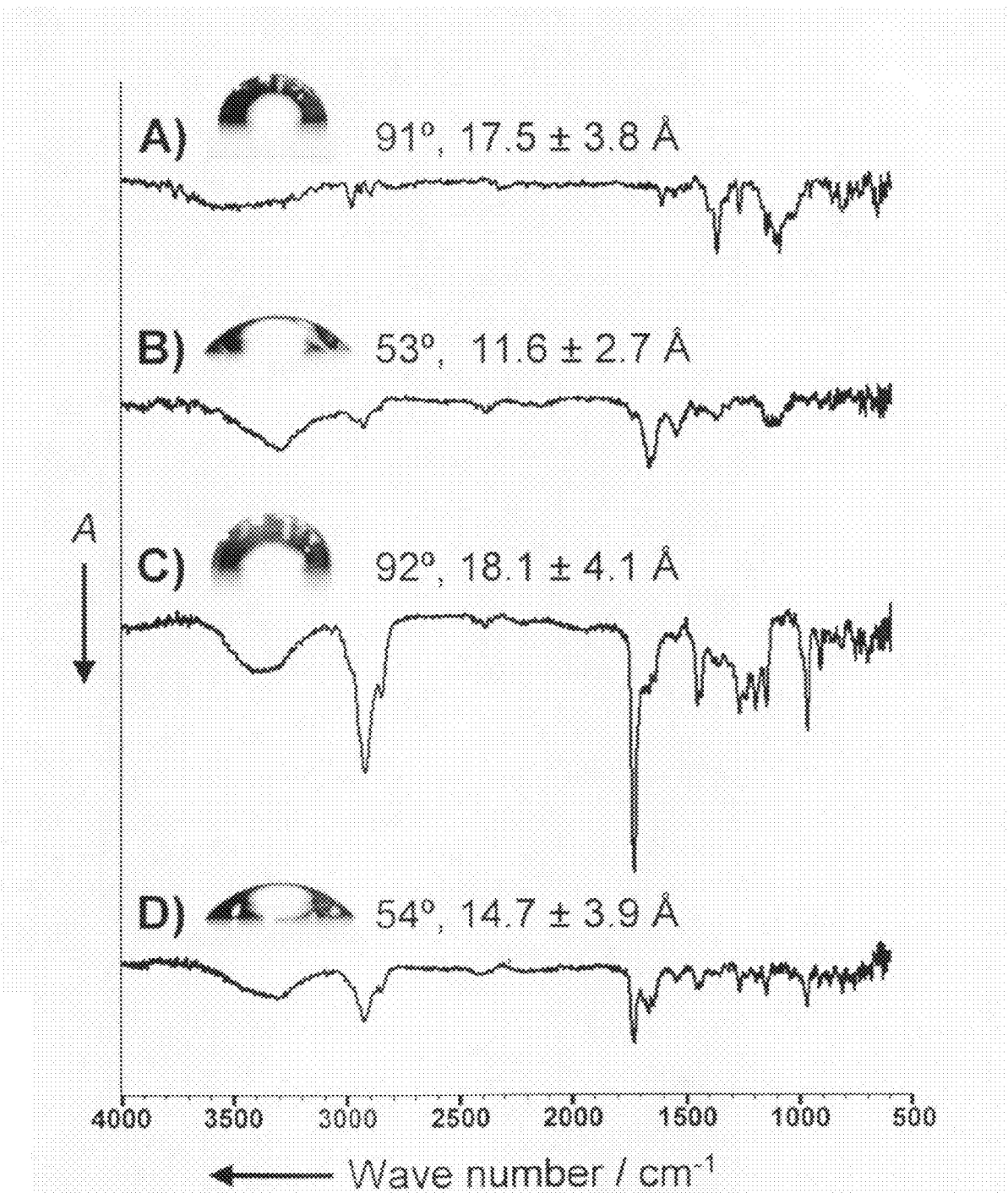
FIG. 13 shows grazing angle FTIR, contact angle, and ellipsometry determined thickness measurements for gold electrodes prepared according to method shown in FIG. 11.

Grazing angle FTIR, ellipsometry, and contact angle measurements were made in order to understand and verify the chemistry of the assembled films and at each step of their chemical manipulation shown in FIG. 11. FIG. 13A shows measurements for phenyl boronic acid pinacol ester surface. FIG. 13B shows measurements for a chemically deprotected boronic acid surface. FIG. 13C shows measurements for a MPMP-diol reprotected surface. FIG. 13D shows measurements for an electrochemically deprotected boronic acid surface. Standard deviations were calculated from 8 or more independent measurements on each of 3 electrodes sampled.

Films of thickness corresponding to approximately 1.7 equivalent monolayers (17.5 Å±3.8 Å) of the phenyl boronic acid pinacolate ester 52 were assembled onto gold from the diazonium precursor using cyclic voltammetry. As expected the contact angle for water on this surface was greater than 90° (FIG. 13A). The FTIR shows CH modes at ca 3000 cm$^{-1}$ and 1090 cm$^{-1}$ and weak aromatic modes at 1609 cm$^{-1}$ and a clear B—O bending mode at 1363 cm$^{-1}$. The FTIR also shows a broad weak O—H stretch at 3500 cm$^{-1}$ presumably due to some inadvertent hydrolysis. After deprotection by periodate, the contact angle of the film drops to 53° as expected for a film 53 with increased hydrophilicity (FIG. 13B). The surface thickness also fell by 5.9 Å, which is near the 3.3 Å length of the pinacol ester blocking group. The FTIR indicates a large increase in the OH stretch relative to the CH modes at 3000 cm$^{-1}$. The deprotection has also enhanced the phenyl ring modes at 1661 cm$^{-1}$. This mode seems to be suppressed by substitution on the boronic acid; it vanishes during reblocking of the boronic acid by the MPMP-diol. Reblocking of the free boronic acid by the MPMP diol (FIG. 13C) is more complicated. Presumably, since the reblocking was performed in anhydrous toluene the product should be trigonal borate. However, inadvertent hydrolysis and steric crowding may result in incomplete borate ester formation. Nonetheless, the contact angle of the reblocked film 55 increased to over 90° and the film thickness increased by elipsometric measurements as expected for the replacement of the pinacol by the larger MPMP-diol 56. Grazing angle FTIR indicates a much weaker OH stretch relative to the CH modes at ca 3000 cm$^{-1}$. Again the substitution of the boronic acid for an ester decreases the strength of the aromatic ring modes. The peak at 1729 cm$^{-1}$ suggests the presence of a ketone. This ketone might be the result from some oxidation of the MPMP diol by trapped periodate (or possibly from the formation of some perborate) and subsequent sequestration in the film. Electrochemical deblocking of the film 57 decreases the contact angle to nearly that of the chemically deblocked film 53 (i.e., compare FIG. 13D to FIG. 13B). Likewise ellipsometry reveals that the film 57 decreased in thickness, but not quite to the original phenyl boronic acid film thickness 53, which again may suggest that some of the oxidation products are trapped in the film. FTIR reveals the 1660 cm$^{-1}$ aromatic mode that seems to reflect that the presence of the free boronic acid is restored. The OH peak again increased in intensity.

Figure 14:
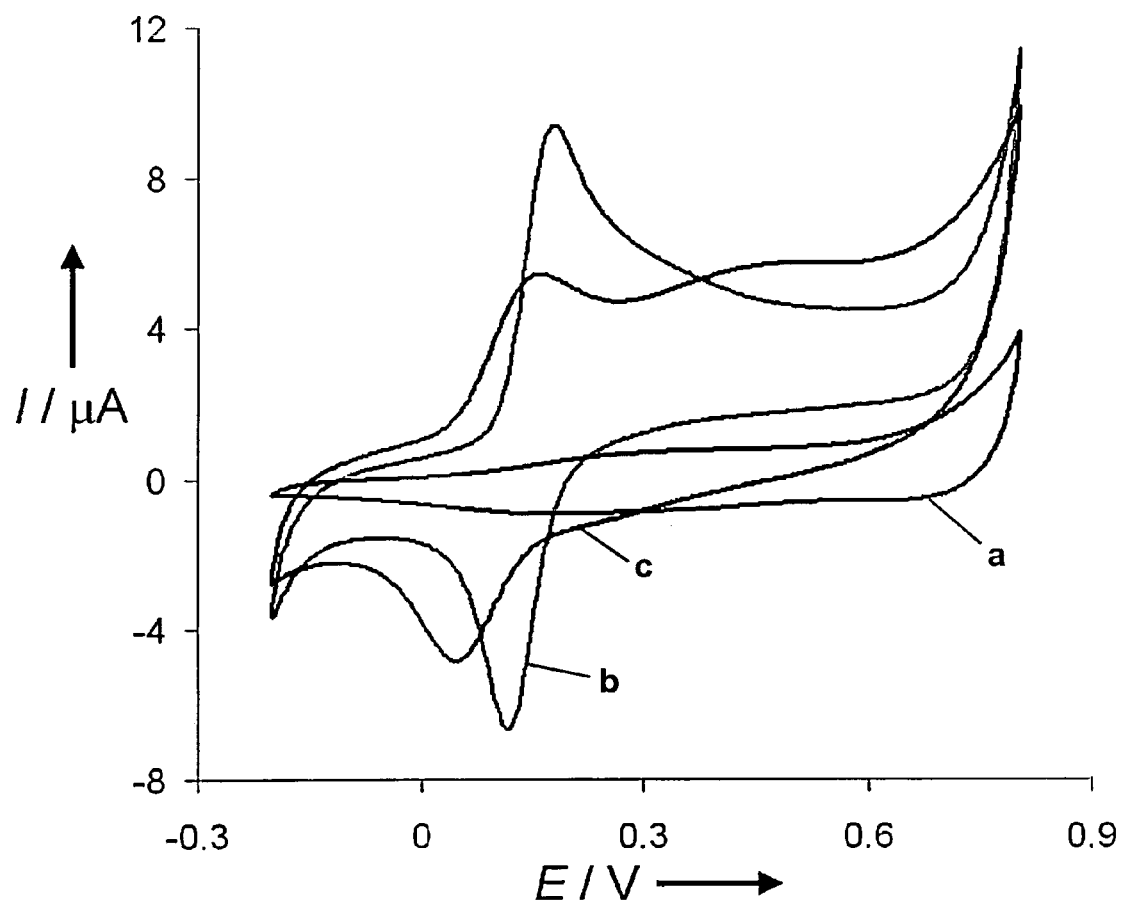
FIG. 14 shows cyclic voltammograms of a phenyl boronic acid modified gold disk electrode in phosphate buffer saline (PBS) solution, pH 7.4 (a), or with 1 mM dopamine in PBS (c). The cyclic voltammetric response of a bare gold disk electrode and with 1 mM dopamine in PBS is shown in (b).

The regeneration of the boronic acid is indirectly verified electrochemically using dopamine oxidation, as shown by the cyclic voltammograms in FIG. 14. The potential scan rate was v=100 mV/sec. Dopamine forms a boronate ester upon reacting with boronic acid that is oxidized at a more positive potential than what is needed to oxidize unconjugated dopamine. No redox peaks were observed in the potential region of interest in a blank phosphate buffer saline solution, pH=7.4, for both the boronic acid surface (a) and the bare gold electrode (not shown). Upon addition of 1 mM dopamine, the bare gold electrode shows a redox couple at 0.19/0.11 V corresponding to the 2 e$^-$, 2 H+ oxidation/reduction of dopamine (b). The phenyl boronic acid-modified electrode showed this same redox couple at 0.098/0.05V and an additional broad oxidation wave centered near 0.48 V (c) which is due to the oxidation of the boronate ester formed between the functional boronic acid groups on the electrode surface and dopamine. This demonstrates the presence of unprotected boronic acid functional groups on the electrode surface.

The affinity for yeast cell adhesion was determined for each of the four surfaces. The prepared electrodes were first conditioned for one hour in 100 mM Tris-HCl, pH 8.5, washed with water and dried with nitrogen. 100 µl of yeast cells (1×10$^7$ cells/ml) or macrophage cells (1-3×10$^7$ cells/ml) in 0.1 M phosphate buffer, pH 7.4, were placed onto the electrodes for two min, and gently washed three times with buffer. A single colony of *S. cerevisiae* strain INVSc1 was inoculated into 5 ml of YPD. The solution was cultured overnight at 30° C. in a shaking incubator at 250 rpm. OD$_{600}$ was measured. The overnight culture was then diluted into fresh YPD to an OD$_{600}$ equal to 0.5 in a total volume of 1 ml of YPD. Murine macrophage strain RAW 264.7 was maintained according to the manufacture protocol. The electrodes were treated with 100 µl of 20 mM fructose in 100 mM Tris-HCl, pH=8.5 for 30 min and washed three times with buffer. The regeneration of the boronic acid groups was accomplished by removing bound fructose with 100 µl of 0.1 M phosphate solution, pH=3.3, for 30 min followed by rinsing with buffer and conditioning the electrodes in 0.1 M Tris-HCl, pH=8.5, for 12 hours.

Figure 15:
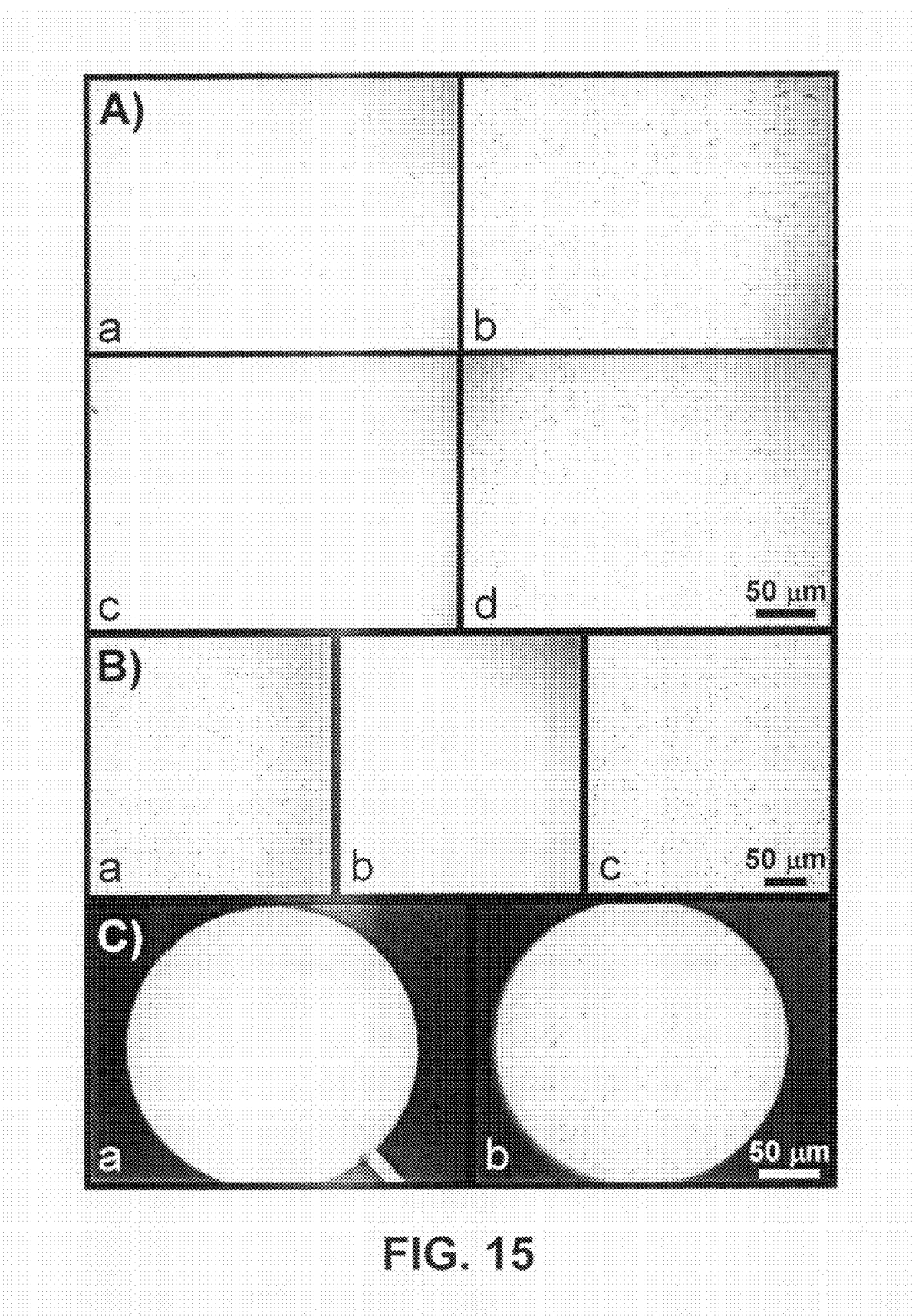
FIG. 15 shows microscope images of gold electrode surfaces exposed to yeast cells. A) Yeast cell adhesion affinity: a) Phenyl boronic acid pinacol ester surface, b) Chemically deprotected boronic acid surface, c) MPMP-diol reprotected surface, d) Electrochemically deprotected boronic acid surface. B) On demand release of yeast cells and surface regeneration: a) Electrochemically deprotected boronic acid surface treated with yeast cells, b) after 30 min treatment with 20 mM fructose solution, c) after low pH regeneration, buffer reconditioning, and treatment with yeast cells. C) Selective patterning of closely spaced arrayed electrodes: a) MPMP-diol reprotected and b) Electrochemically deprotected boronic acid individually addressable electrodes after simultaneous treatment with yeast cells.

In FIG. 15A are shown microscope images of each prepared electrode. The images show cells adhere only to the de-blocked boronic acid surfaces (b and d) while very few cells have non-specifically bound to the two blocked surfaces (a and c) showing activity consistent with the steps shown in FIG. 11, and in agreement with the contact angle and FTIR data shown in FIG. 13. Adhesion of the yeast cells was stable overnight.

Competitive binding of sugars was examined as a possible method for cell detachment. Fructose, in particular, has a particularly high affinity for aryl boronic acids in the pH range 7-9. A prepared electrode, electrochemically deblocked, exposed to yeast cells, and then incubated for 30 min with 20 mM fructose, 100 mM Tris-HCl, pH 8.5 indicated an almost complete removal of cells, as shown in FIG. 15B (a and b, respectively). Bound fructose was then removed by treatment with phosphate solution, pH 3. After reconditioning with 100 mM Tris-HCl, pH 8.5, and exposure to yeast cells, the apparent activity of the boronic acid groups seems unaffected, as indicated by the subsequent reattachment of cells, as shown in FIG. 15B(c). The ability to release the attached cells via a fructose treatment, and regeneration of the surface for subsequent cellular adhesion indicates that this electrode can be used as a reusable platform for cell capture with on-demand release.

The utility of this technique to selectively immobilize cells in an array format is presented in FIG. 15C. Two closely-spaced individually addressable 0.5 mm gold disk electrodes were modified up to step 3, reprotected electrode 55, as shown in FIG. 11. One electrode was oxidatively treated at 0.6 V for 1 min in 50 mM phosphate buffer, pH 7.4, to de-protect the boronic acid group, and both were exposed to the same yeast cell solution. As can be seen in the microscope pictures, the blocked electrode 55 in FIG. 15C(a) shows few cells adhere to the surface while the electrochemically de-protected electrode 57 in FIG. 15C(b) shows excellent cell adhesion properties. The replacement of the methoxy group of the MPMP diol with a short ethoxylate chain can further improve the selectivity by decreasing the effects of nonspecific binding. Ethoxylated surfaces are well known to decrease the formation of biological films. This electrochemical activation of a boronic acid surface allows a great deal of control over the spatial confinement of cells in biosensors which contain a high density of working electrodes. This method enables more complex cellular studies by providing a simple method to pattern differing cell types on closely spaced arrayed electrodes, or the modification of electrodes near the captured cells with chemical or biological sensitive groups which can monitor the cells' environment or response to stimuli in real time.

Figure 16:
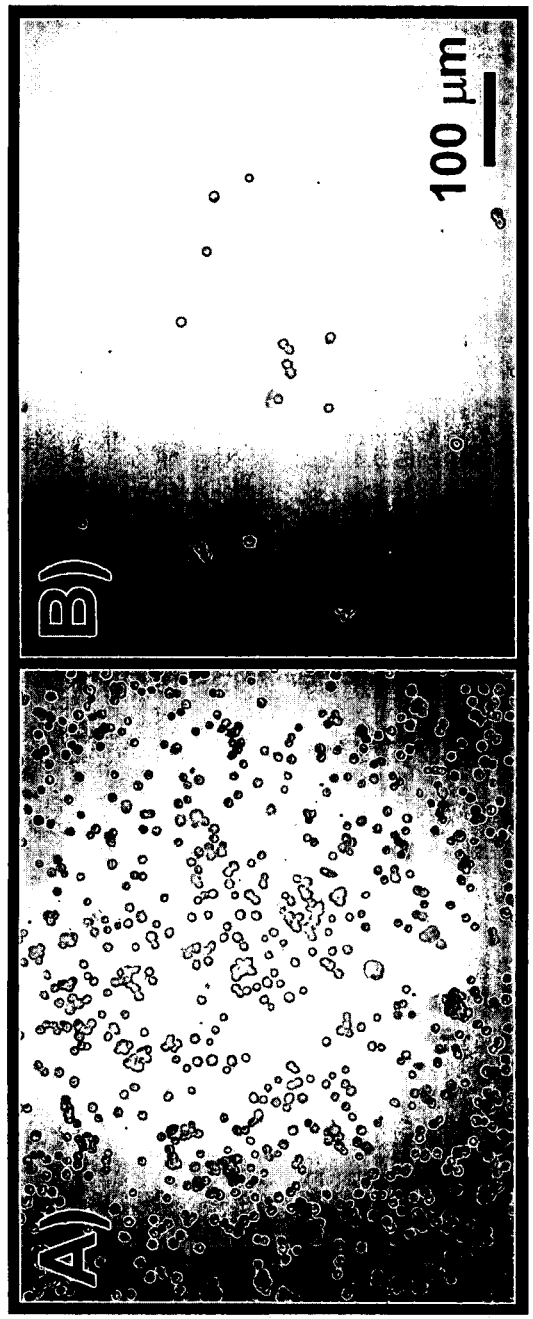
FIG. 16 shows microscope images of gold electrode surfaces exposed to mammalian macrophage cells: A) Capture of macrophage cells on a phenyl boronic acid surface and B) On-demand release after 30 min treatment with 20 mM fructose solution.

The method is also compatible with more sensitive and relevant mammalian cells. Murine macrophage cells were immobilized onto a phenyl boronic acid modified gold electrode, as shown in FIG. 16A, using the same protocol as described for yeast immobilization. A treatment of the surface in fructose solution was again successful in releasing the captured cells, as shown in FIG. 16B. Additionally, captured cell viability was monitored (in 1×PBS buffer, pH 7.4, at 37° C.) 30, 60, and 120 minutes post immobilization. These time frames are relevant to many cell-cell and cell signaling interaction studies. After 30 minutes, roughly 3±1% of the immobilized cells had died. After 60 minutes an additional 3±2% of cells died. Finally, after 120 minutes approximately 13±4% if the cells had died. Death is likely due to the lack of defined nutrients in the buffer solution and can be minimized by determining which media components can be added to the buffer without affecting cellular immobilization to the boronic acid surface. Still, nearly 80% of the immobilized cells remain viable over 2 hours in buffer immobilized onto the gold electrodes demonstrating the utility of this method for many diverse cell based studies.

The present invention has been described as a method for preparing an electrochemical biosensor by the electro-addressable functionalization of electrode arrays. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for preparing an electrochemical biosensor, comprising:
    (i) providing an electrode array comprising a plurality of conducting or semiconducting electrodes;

(ii) grafting a phenyl boronic acid diazonium salt having an unreactive group to the plurality of electrodes to form an assembly comprising a phenyl molecule comprising an unreactive group, wherein step (ii) comprises bias-assisted electrodeposition of the phenyl boronic acid diazonium salt to the plurality of conducting or semiconducting electrodes and wherein the bias-assisted electrodeposition comprises use of a first bias voltage; and (iii) applying a second bias voltage to at least one electrode of the plurality of conducting or semiconducting electrodes to convert the unreactive group of the phenyl molecule to a reactive group;

wherein the reactive group comprises a chemical or biological recognition group that has selectivity for a target analyte.

2. The method of claim 1, wherein grafting the phenyl boronic acid diazonium salt in step (ii) comprises use of a chronoamperometry method or a linear sweep method to provide the first bias voltage.

3. The method of claim 1, wherein the unreactive group comprises a nitro or methoxybenzyl group.

4. The method of claim 3, wherein applying the second bias voltage in step (iii) comprises unblocking or deprotecting the unreactive group to convert the unreactive group to the reactive group.

5. The method of claim 1, wherein the reactive group comprises an amine, carboxyl, boronic acid, maleimide, thiol, biotin, or avidin group.

6. The method of claim 1, further comprising:
(iv) reacting the reactive group with a chemical or biological recognition molecule to provide the chemical or biological recognition group that has selectivity for the target analyte.

7. The method of claim 6, wherein the recognition molecule comprises a native, modified, or synthetic biological molecule or a chemical molecule.

8. The method of claim 6, wherein the recognition molecule comprises an antibody, protein, enzyme, saccharide, DNA, RNA, peptide, or whole cell.

9. The method of claim 6, wherein the recognition group comprises an amine, carboxyl, boronic acid, maleimide, thiol, biotin, or avidin group.

10. The method of claim 6, wherein the unreactive group is blocked, protected, or inactive toward to the recognition molecule.

11. The method of claim 1, wherein grafting the phenyl boronic acid diazonium salt in step (ii) comprises bias-assisted electrodepositing phenyl boronic acid pinacol ester diazonium on the plurality of electrodes, chemically deprotecting the pinacol ester blocking group of the deposited phenyl molecules with an oxidant thereby forming a phenyl boronic acid, and reprotecting the phenyl boronic acid with an unreactive methoxybenzyl group.

12. The method of claim 11, further comprising:
(iv) reacting the reactive group of the phenyl boronic acid with one or more cells to provide reversible cell immobilization on the electrochemical biosensor.

13. The method of claim 12, further comprising:
(v) treating the electrode array with a sugar to release one or more attached cells, thereby regenerating a surface of the electrochemical biosensor.

14. A method for preparing an electrochemical biosensor, comprising:
(i) providing an electrode array comprising a plurality of conducting or semiconducting electrodes;
(ii) grafting a phenyl boronic acid diazonium salt having an unreactive group to the plurality of electrodes to form an assembly comprising a phenyl molecule comprising an unreactive group, wherein step (ii) comprises bias-assisted electrodeposition of the phenyl boronic acid diazonium salt to the plurality of conducting or semiconducting electrodes and wherein the bias-assisted electrodeposition comprises use of a first bias voltage;
(iii) applying a second bias voltage to at least one electrode of the plurality of conducting or semiconducting electrodes to convert the unreactive group of the phenyl molecule to a reactive group; and
(iv) reacting the reactive group with a chemical or biological recognition molecule to provide a chemical or biological recognition group that has selectivity for a target analyte.

15. The method of claim 14, wherein grafting the phenyl boronic acid diazonium salt in step (ii) comprises bias-assisted electrodepositing of the phenyl boronic acid diazonium salt on the plurality of electrodes, chemically deprotecting the deposited phenyl molecules with an oxidant thereby forming a phenyl boronic acid, and reprotecting the phenyl boronic acid with an unreactive group.

\* \* \* \* \*